(12) United States Patent
Cheung et al.

(10) Patent No.: US 7,339,043 B2
(45) Date of Patent: Mar. 4, 2008

(54) COMPOSITIONS AND METHODS FOR AFFECTING VIRULENCE DETERMINANTS IN BACTERIA

(75) Inventors: Ambrose L. Cheung, Hanover, NH (US); Adhar Manna, Lebanon, NH (US)

(73) Assignee: Trustees of Dartmouth College, Hanover, NH (US)

( * ) Notice: Subject to any disclaimer, the term of this patent is extended or adjusted under 35 U.S.C. 154(b) by 0 days.

(21) Appl. No.: 11/063,308

(22) Filed: Feb. 22, 2005

(65) Prior Publication Data

US 2005/0239704 A1 Oct. 27, 2005

Related U.S. Application Data

(63) Continuation of application No. 10/043,539, filed on Jan. 11, 2002.

(60) Provisional application No. 60/261,233, filed on Jan. 12, 2001, provisional application No. 60/261,607, filed on Jan. 12, 2001, provisional application No. 60/289,601, filed on May 8, 2001.

(51) Int. Cl.
| | |
|---|---|
| *C07H 21/02* | (2006.01) |
| *C07H 21/04* | (2006.01) |
| *A61K 39/00* | (2006.01) |
| *A61K 39/09* | (2006.01) |
| *A61K 39/085* | (2006.01) |

(52) U.S. Cl. .............. 536/23.1; 536/23.7; 424/184.1; 424/237.1; 424/243.1

(58) Field of Classification Search ............. 424/184.1, 424/237.1, 243.1; 536/23.1, 23.7
See application file for complete search history.

(56) References Cited

OTHER PUBLICATIONS

Heinrichs et al (Journal of Bacteriology, Jan. 1996, p. 418-423).*
Bayer et al (Journal of Bacteriology, Aug. 1996, p. 4563-4570).*
Manna et al (Infection and Immunity, Aug. 1998, p. 3828-3836).*
Manna et al (Infection and Immunity, Feb. 2001, p. 885-896).*
(NCBI Database, Genebank, Accession No. AF207701 date created Dec. 1, 2000).*
Bayer et al., "The Molecular Architecture of the *sar* Locus in *Staphylococcus aureus*", Journal of Bacteriology 1996 178 (15):4563-4570.
Cheung et al., "Regulation of exoprotein expression in *Staphylococcus aureus* by a locus (*sar*) distinct from *agr*", Proc. Natl. Acad. Sci. USA 1992 89:6462-6466.
Cheung et al., "Cloning and Sequencing of *sarA* of *Staphylococcus aureus*, a Gene Required for the Expression of *agr*", Journal of Bacteriology 1994 176(13):4168-4172.
Cheung et al., "*sar* Genetic Determinants Necessary for Transcription of RNAII and RNAIII in the *agr* Locus of *Staphylococcus aureus*", Journal of Bacteriology 1997 179(12):3963-3971.
Manna et al., "Transcriptional Analysis of Different Promoters in the *sar* Locus in *Staphylococcus aureus*", Journal of Bacteriology 1998 180(15):3828-3836.
Manna et al., "Characterization of *sarR*, a Modulator of *sar* Expression in *Staphylococcus aureus*", Infection and Immunity 2001 69(2):885-896.
Tegmark et al., "Identification and characterization of SarH1, a new global regulator of virulence gene expression in *Staphylococcus aureus*", Molecular Microbiology 2000 37(2):398-409.

* cited by examiner

*Primary Examiner*—Jeffrey Siew
*Assistant Examiner*—Vanessa L. Ford
(74) *Attorney, Agent, or Firm*—Licata & Tyrrell P.C.

(57) ABSTRACT

A novel sarR gene and sarR gene product which down regulates the expression of sarA and the resulting virulence determinants in *Staphylococcus aureus* is provided. Methods for modulating the expression of sarA and virulence determinants are also provided. A preferred embodiment of the present invention provides structural information relating to the gene product and enables the identification and formulation of lead compounds and reducements for treating and preventing infections by *S. aureus* and related bacteria.

5 Claims, 13 Drawing Sheets
(4 of 13 Drawing Sheet(s) Filed in Color)

FIG. 1B

```
  1 GTTTTCAAAA TCGGTGGAGG TGCATGAAAA AGTTATTGGG
 41 CATTTTTTGA AAATAAAAAA ATATCAATAA GTTGGAGTCA
                                        ↓START
 81 TTACCGAATT TTTATACTTA TTTGTTTAGA ATGAACTTTA
    ‾‾‾‾‾‾‾‾‾‾                         ‾‾‾‾‾‾‾‾‾‾
       -35                                -10
121 TAACATAGTT GGATAGAGTT TTCGATTTAA TACATTAAAT
161 GTGAACCTTG CTACAACAAG ATGTGCATCA GAAGGAGTGG
                                       ‾‾‾‾‾‾‾‾‾
                                   RIBOSOME BINDING SITE
201 TTTAATAATG --sarR--TAA (SEQ ID NO:19)
```

FIG. 1C

```
                10        20        30         40
SarR    M--SKINDINDLVNATFQVKKFFRDTKKKFNLNYEEIYILN
         . .::::   .:..  . :    ::.:........::. .:.
SarA    MAITKINDCFELLSMVTYADKLKSLIKKEFSISFEEFAVLT 50        60        70         80
SarR    HILRSESNEISSKEIAKCSEFKPYYLTKALQKLKDLKLLS
         .: ... .:    :.:  .  ..:    ..::.. :..   ..
SarA    YISENKEKEYYLKDIINHLNYKQPQVVKAVKILSQEDYFD 90        100        110
SarR    QKRILQDERTVIVYVT-------DTLKANIHKLISELEEY
         .::  .::::::.. :.            ..: . ..:  :.:. ..
SarA    KKRNEHDERTVLILVNAQQRKKIESLLSRVNKRITEANNE

SarR    IKN (SEQ ID NO:2)
         :.
SarA    IEL (SEQ ID NO:3)
```

FIG. 2

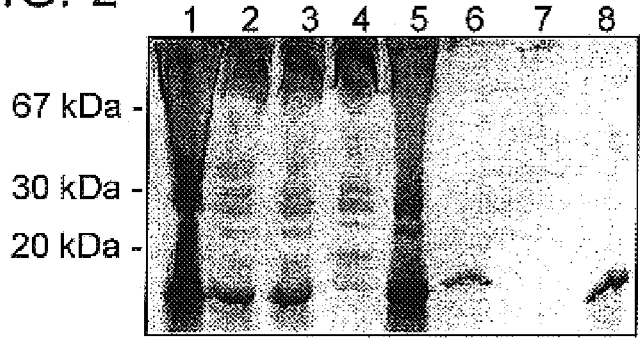

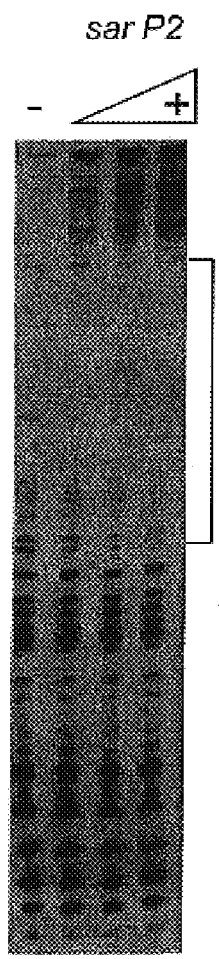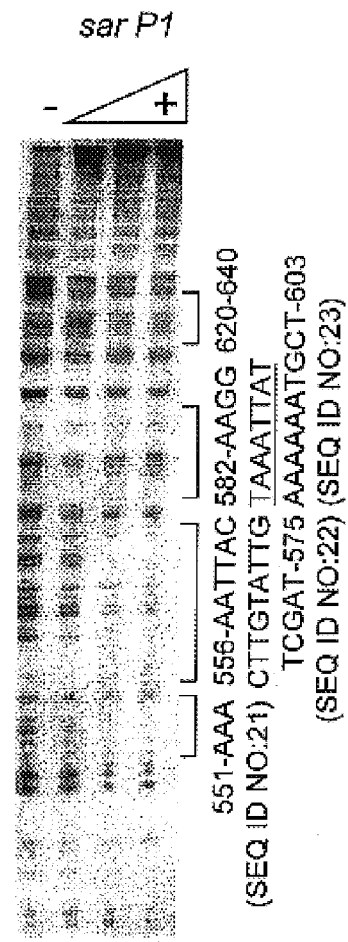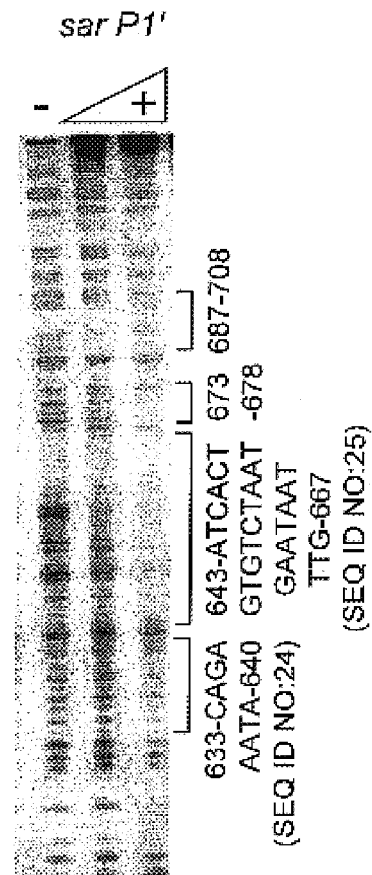
FIG. 5A sar P2
FIG. 5B sar P1
FIG. 5C sar P1'

90° Canyon

90°

US 7,339,043 B2

COMPOSITIONS AND METHODS FOR AFFECTING VIRULENCE DETERMINANTS IN BACTERIA

This application is a continuation of U.S. Ser. No. 10/043,539, filed Jan. 11, 2002, which claims priority to U.S. Provisional Application Ser. No. 60/261,233, filed Jan. 12, 2001, U.S. Provisional Application Ser. No. 60/261,607 filed Jan. 12, 2001, and U.S. Provisional Application Ser. No. 60/289,601, filed May 8, 2001. These applications are hereby incorporated by references herein in their entirety.

FIELD OF THE INVENTION

The present invention relates generally to the field of molecular biology. More particularly, certain embodiments concern methods and compositions comprising DNA segments and protein derived from *Staphyloccocus aureus* and other bacterial species. The present invention also relates to the three-dimensional structure of proteins derived from *S. aureus* and other bacterial species and methods of identifying and developing pharmaceuticals using, among other things, drug screening assays.

BACKGROUND OF THE INVENTION

Throughout this application, various publications are referenced by Arabic numerals within parentheses. Full citations for these publications is found at the end of the specification immediately preceding the claims. The disclosures of these publications in their entireties are hereby incorporated by reference into this application.

Bacterial infections are a serious problem in humans. In the past decade, the number of "supergerms" that resist treatment has increased dramatically. Unfortunately, the very same arsenal of drugs used to overcome these microbes helped give rise to antibiotic-resistant strains of bacteria. Of great importance are several antibiotic-resistant and sometimes fatal bacteria including *S. aureus, Pseudomonas aeruginosa* (pneumonia), and *Enterococcus faecalis* (urinary tract and blood infections).

For most healthy people, these antibiotic-resistant bacteria are not life-threatening. The immune system, the body's natural defense against microbes, usually fights off disease-causing bacteria. However, when bacteria attack people with weakened immune systems they can be deadly. Hailed as miracle drugs, antibiotics have cured thousands of bacterial infections, from acne to strep throat to ear infections. Today, there are more than 100 types of antibiotics on the U.S. market. Due to increasing resistance to antibiotics, however, new treatments are still needed.

In particular, *S. aureus* infections have been problematic to treat. *S. aureus* are non-mobile, non-sporulating gram-positive cocci 0.5-1.5 µm in diameter, that occur singly and in pairs, short chains, and irregular three-dimensional grape-like clusters. *S. aureus* can grow over a wide range of environmental conditions, but they grow best at temperatures between 30° C. and 37° C. and at a neutral pH. They are resistant to desiccation and to chemical disinfection, and they tolerate NaCl concentrations up to 12%. It has been found that the growth of *S. aureus* becomes unusually sensitive to high NaCl concentrations (by decreasing $Ca^{2+}$ concentration) in growth media allowing for autolysis (29).

*S. aureus* can cause a wide spectrum of infections ranging from superficial abscesses; pneumonia and endocarditis to sepsis (4). The ability of *S. aureus* to cause a multitude of human infections is due, in part, to an impressive array of extracellular and cell-wall associated virulence determinants that are coordinately expressed in this organism (51). The coordinate expression of many of these virulence determinants in *S. aureus* and other bacteria is regulated by global regulatory elements such as sarA and agr (15, 34). These regulatory elements, in turn, control the transcription of a wide variety of unlinked genes many of which have been implicated in pathogenesis.

The global regulatory locus agr encodes a two-component, quorum sensing system that is involved in the generation of two divergent transcripts, RNAII and RNAIII, from two distinct promoters, P2 and P3, respectively. RNAIII is the regulatory molecule of the agr response, hence responsible for the up-regulation of extracellular protein production and down-regulation of cell-wall associated protein synthesis during the postexponential phase (39,49). The RNAII molecule, driven by the P2 promoter, encodes a four-gene operon, agrBDCA, with AgrC and AgrA corresponding to the sensor and activator proteins of a two component regulatory system. Additionally, agrD, in concert with agrB, participates in the generation of an octapeptide with quorum sensing functions (31,41). The autoinducing peptide would stimulate the transcription of the agr regulatory molecule RNAIII which ultimately interacts with target genes to modulate transcription (49) and possibly translation (44).

In contrast to agr, the sarA locus activates the synthesis of both extracellular (e.g. α- and β-hemolysins) and cell-wall proteins (e.g. fibronectin binding protein) in *S. aureus* (15). The sarA locus is composed of three overlapping transcripts [sarA P1 (0.56 kb), sarA P3 (0.8 kb) and sarA P2 (1.2 kb) transcripts], each with a common 3' end but initiated from three distinct promoters (P1, P3 and P2 promoters). Due to their overlapping nature, each of these transcripts encodes the major 372-bp sarA gene, yielding the 14.5 kDa sarA protein (2). DNA footprinting studies have shown that the sarA protein binds to the promoters of several target genes (19) including agr, hla (alpha hemolysin gene), spa (protein A gene) and fnbA (fibronectin binding protein A gene), thus implicating sarA as a regulatory molecule that can modulate target gene transcription via both agr-dependent and agr-independent pathways (9,19,20). With agr-dependent pathway of target gene activation, the sarA protein binds to the agr promoter to stimulate RNAIII transcription and RNAIII, in turn, interacts with target genes (e.g. hla) to modulate transcription. With sarA-dependent but agr-independent pathway, the SarA protein will interact directly with target-gene promoters (e.g. hla and spa) (19) to control gene transcription. Deletion and promoter fusion analyses indicates that the regions upstream of the sarA P2 and between the P1 and P3 promoters have a modulating role in sarA expression, possibly by controlling transcription from the sarA P1 promoter, the predominant promoter within the sarA locus (10,39) (FIG. 1A).

A great need exists for methods and compositions which can affect or regulate the virulence of bacteria, such as the expression of sarA and the resultant virulence determinants of *S. aureus* and other bacteria.

SUMMARY OF THE INVENTION

The present invention provides a new genetic locus of *S. aureus* and other bacteria. The gene at this locus is referred to herein as sarR. The sarR gene is involved in the regulation and expression of virulence determinants in *S. aureus* and other bacteria.

The present invention provides a polynucleotide sequence of the sarR gene (SEQ. ID. NO: 1) which is involved in the regulation and expression of virulence determinants in S. aureus and related bacteria. Also provided is a sarR gene product, an isolated polypeptide which is involved in regulation and expression of virulence determinants in S. aureus and related bacteria.

An object of the present invention is to provide nucleic acid sequences that regulate the expression of virulence determinants in S. aureus and related bacteria. In a preferred embodiment the nucleic acid sequence is isolated from S. aureus and in another preferred embodiment the nucleic acid sequence is a sarR gene (SEQ. ID. NO: 1).

Another object of the present invention is to provide a polypeptide which regulates the expression of virulence determinants in S. aureus and other bacteria. In a preferred embodiment the polypeptide is isolated from S. aureus and in another preferred embodiment the polypeptide is encoded by a sarR gene and correspond to the sequence set forth in SEQ ID NO: 2.

Vectors and host cells comprising nucleic acid sequences encoding these polypeptides and chemical entities that mimic or enhance the activity of such polypeptides are further objects of the invention. These agents can be used alone or in combination with antibacterial agents such as penicillin to enhance the properties of such agents.

Another object of the present invention is to provide methods for modulating regulation and expression of virulence determinants in S. aureus and related bacteria to inhibit their growth and infectivity by contacting the bacteria with an agent which interacts with sarA promoter regions.

Another object of the present invention is to provide a method of inhibiting growth and infectivity of bacteria comprising contacting the bacteria with an agent which enhances the expression of the sarR gene, or the activity of a polypeptide encoded by the sarR. gene.

Another object of the present invention is to provide a kit for identifying the presence of a sarR gene or a polypeptide encoded by a sarR gene.

A further object of the present invention is to provide nucleic acid sequences from a mutant sarR gene in S. aureus and related bacteria, and polypeptides encoded by a mutant sarR gene.

A further object of the invention is to provide a three dimensional crystal structure of the SarR protein.

A further object of the invention is to provide methods of screening for lead compounds which inhibit the expression of virulence determinants in S. aureus and related bacteria.

Another object of the present invention is to provide pharmaceutical compositions for use as anti-bacterial agents against S. aureus and other bacteria.

BRIEF DESCRIPTION OF THE DRAWINGS

The file of this patent contains at least one drawing executed in color.

FIG. 1B shows the promoter region of sarR. The transcription start site has been mapped by primer extension to position 119. Examples of −10 and −35 promoter boxes are in bold and underlined.

FIG. 1C shows the alignment of SarR with SarA. Colon represents identity while a period indicates conservative substitution.

FIG. 2 demonstrates purification of sarR from the pET11b expression vector.

FIG. 5 shows DNaseI footprinting assays of sarR with end-labeled $^{32}$P sar P2 (49-bp fragment), P1 (nt 531-859) and P1' (nt 620-859) promoter fragments.

FIG. 6 shows the expression of sarR in parental strain RN6390 and its sar (ALC488) and agr (RN6911) mutants.

FIG. 8 demonstrates the effect of the sarR mutation on sarA and agr expression.

FIG. 12A illustrates the potential surface of the concave side of SarR dimer (similar orientation as FIG. 10A). The direct line distance of AB is ~65Å; the distance of the inner surface covered by AB is 90° A. FIG. 12B illustrates the potential surface of the convex side of the SarR dimer (similar orientation as FIG. 10C). Two aspartic acid residues are from one molecule, three glutamic acid residues from the other.

DETAILED DESCRIPTION OF THE INVENTION

Figure 1A:
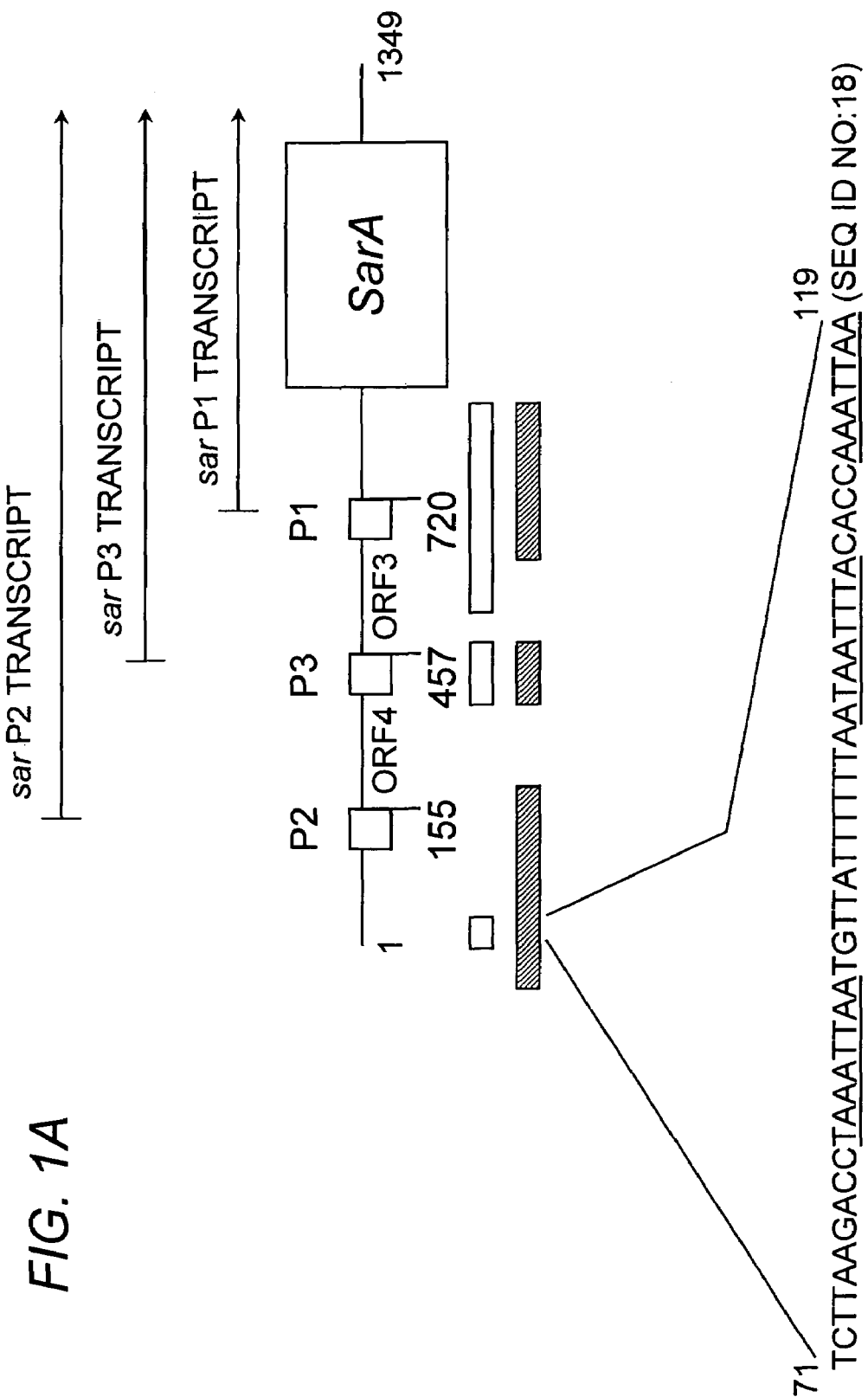
FIG. 1A illustrates a schematic of the sar promoters and transcripts.
Figure 3A:
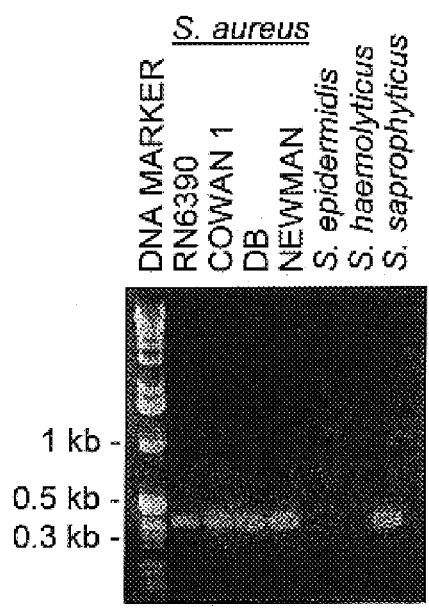
FIG. 3A demonstrates PCR amplification of sarR-like genes in S. aureus strains RN6390, Cowan I, D B and Newman, S. epidermidis, S. haemolyticus and S. saprophyticus.
Figure 3B:
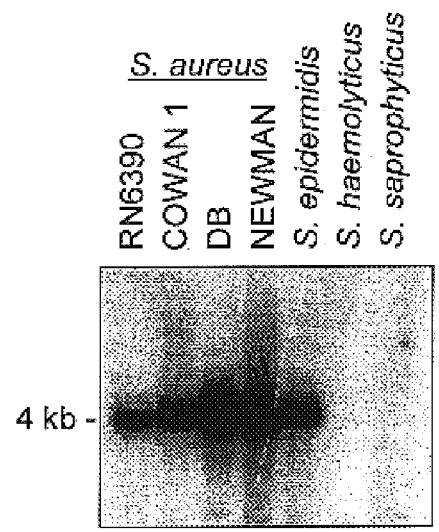
FIG. 3B shows a Southern blot of the strains in FIG. 3A above strain restricted with ClaI and probed with a 345-bp sarR probe (nt 208-552).
Figure 3C:
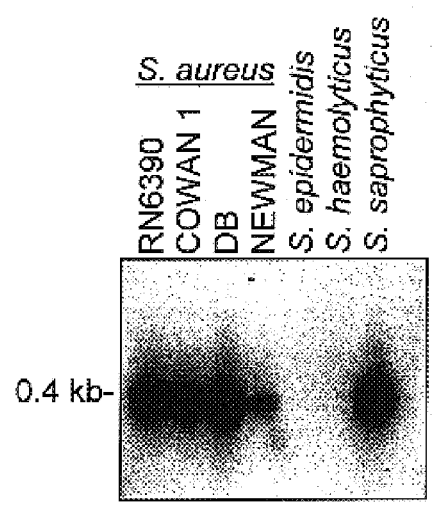
FIG. 3C shows a Northern blot of the total cellular RNA (10 µg each) of the strains of FIG. 3D probed with a sarR probe.
Figure 3D:
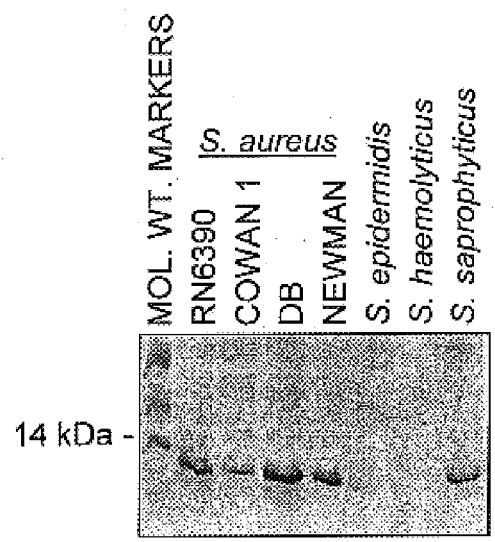
FIG. 3D shows cell lysates of the above strains immunoblotted onto nitrocellulose and probed with anti-sarR monoclonal antibody 2A7 at a 1:2000 dilution.

If appearing herein, the following terms shall have the definitions set out below.

As used herein, the term "gene" refers to an assembly of nucleotides that encode a polypeptide, and includes cDNA and genomic DNA nucleic acids.

A "vector" is a replicon, such as plasmid, phage or cosmid, to which another DNA segment is attached so as to bring about the replication of the attached segment.

A DNA "coding sequence" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site as well as protein binding domains (consensus sequences) responsible for the binding of RNA polymerase.

As used herein, the term "homologous" in all its grammatical forms refers to the relationship between proteins that possess a "common evolutionary origin," including proteins from superfamilies and homologous proteins from different species. Such proteins have sequence homology as reflected by their high degree of sequence similarity. Preferably, homologous gene sequences will have at least 50% sequence identity (as defined by the maximal base match in a computer-generated alignment of two nucleic acid sequences), more preferably at least 60%, and most preferably at least 80%. For polypeptide gene products of such homologous genes, generally the gene products also exhibit a significant degree of amino acid sequence identity. Thus, for such polypeptide products of homologous genes, the amino acid sequences have at least 25% sequence identity over a sequence of 100 or more amino acids, more preferably at least 40%, still more preferably at least 60%, and most preferably at least 80%. In addition, in the present context, the products of the homologous gene sequences are also involved in regulation of sarA expression. Thus, the present invention applies as well to bacteria having significant sequence, structural, or functional homology to the sarR gene or SarR protein.

Accordingly, the term "sequence similarity" in all its grammatical forms refers to the degree of identity or correspondence between nucleic acid or amino acid sequences of proteins that may or may not share a common evolutionary origin However, in common usage and in the instant application, the term "homologous," when modified with an adverb such as "highly," may refer to sequence similarity and not a common evolutionary origin.

The term "corresponding to" is used herein to refer similar or homologous sequences, whether the exact position is identical or different from the molecule to which the similarity or homology is measured. Thus, the term "corresponding to" refers to the sequence similarity, and not the numbering of the amino acid residues or nucleotide bases.

The term "a sequence essentially as set forth in SEQ ID NO:-" means that the sequence substantially corresponds to a portion of SEQ ID NO:-" and has relatively few amino acids that are not identical to, or a biologically functional equivalent of, the amino acids of SEQ ID NO:-. Accordingly, sequences that have between about 70% and about 80%; or more preferably, between about 81% and about 90%; or even more preferably, between about 91% and about 99%; of amino acids that are identical or functionally equivalent to the amino acids of SEQ ID NO:-- will be sequences that are "essentially as set forth in SEQ ID NO:-."

Typically, though not necessarily, a ligand in the context of this invention is a molecule with a molecular weight of less than 10,000 daltons, more typically less than 5,000 daltons.

As used herein "related bacterial species" refer to bacterial species having a gene corresponding to the sequence as essentially set forth in SEQ ID NO: 1, and analogs or homologs thereof. Related bacteria according to the present invention include *S. aureus* strains RN6390, Newman, Cowan I and DB and *S. saprophyticus*.

The present invention provides a novel gene found in *S. aureus* and other bacterial species. This gene is designated herein as sarR and is represented SEQ ID NO: 1. The present invention also provides for a novel gene corresponding to the sequence as essentially set forth in SEQ ID NO: 1, and analogs or homologs thereof.

The present invention also provides the sarR gene product designated herein as the SarR protein represented in SEQ ID. NO: 2, and analogs or homologs thereof. The SarR protein has a molecular weight of approximately 13.7 kDa and has a deduced basic pI of approximately 9.2. The sarR gene product is also characterized by a predominance of charged residues (34%).

The present invention also relates to newly discovered binding sites in the sarA promoter system. These binding sites enable the SarR protein to repress sarA expression by preventing sarA from initiating the expression of virulence factors The present invention further provides a model for a SarA/SarR heterodimer which interferes with the function of the SarA homodimer. The present invention also provides alternative heterodimers which include SarA/SarR peptidomimetic combinations and other combinations resulting from lead compounds developed from structural analysis of SarR.

The present invention also provides a sarR gene product or peptidomimetic capable of directly binding to promoters of a virulence gene such as the hla promoter of the alpha hemolysin gene to provide direct inhibition of such virulence factors.

The present invention also provides a method of down; regulating sarA P1 transcription to repress the expression of sarA. This function of the sarR gene product was demonstrated by the results of mutant studies disclosed herein. The sarR mutant expressed a much higher level of the SarA protein than the parent strain. Accordingly, the present invention also provides sarR mutant strains. These strains are useful as experimental and diagnostic tools to specifically characterize the sarA expression systems.

The present invention also provides a detailed three-diminsional (3-D) crystal structure of the SarR protein. The structural data demonstrate that the protein is a member of a new family of winged helix proteins.

The present invention provides methods for treating microbial pathogenesis by the administration of SarR analogs in the form of small molecule compounds which alter the functioning of a microbial sarA expression. Reducing or eliminating the expression of sarA by such analogs can greatly alter the course and effects of a bacterial infection. This treatment approach is distinct from most prior bactericidal or bacteristatic antimicrobial treatments which attempted to either kill the microbial cells, or directly prevent them from reproducing. The antimicrobial action of the compounds of these standard antimicrobial treatments is exerted both in vivo, in an infection, and in vitro, in a culture, unless some specific compensating factor(s) is provided which allows survival or growth in the presence of the antimicrobial agent. In contrast, this invention is directed at the regulation of sarA expression which is involved in the pathogenesis process, but is not necessarily essential for microbial survival or growth in vitro. By selectively targeting the expression of virulence factors and not directly killing the bacterium there is less pressure to develop antimicrobial resistance. Because this type of therapy is less likely to alter the local flora, the incidence of superinfection (e.g. fungal or other bacterial infections such as pseudomonas or enterococcus) is reduced.

According to one aspect of the present invention, an analog library is provided to produce a very large number of potential molecules for regulating the sarA expression system, and in general the greater:the number of analogs in the library, the greater the likelihood that at least one member of the library will effectively regulate the sarA expression system. Designed libraries following a particular template structure and limiting amino acid variation at particular positions are much preferred, since a single library can encompass all the designed analogs and the included sequences will be known and presented in roughly equal numbers. By contrast, random substitution at only six positions in an amino acid sequence provides over 60 million analogs, which is a library size that begins to present practical limitations even when utilizing screening techniques as powerful as phage display. Libraries larger than this would pose problems in handling, e.g., fermentation vessels would need to be of extraordinary size, and more importantly, the likelihood of having all of the planned polypeptide sequence variations represented in the prepared library would decrease sharply. It is therefore preferred to create a designed or biased library, in which the amino acid positions designated for variation are considered so as to maximize the effect of substitution on the sarA regulation characteristics of the analog, and the amino acid residues allowed or planned for use in substitutions are limited.

The use of replicable genetic packages, such as the bacteriophages, is one method of generating novel polypeptide entities that regulate sarA expression. This method generally consists of introducing a novel, exogenous DNA segments into the genome of a bacteriophage (or other amplifiable genetic package) so that the polypeptide encoded by the non-native DNA appears on the surface of the phage. When the inserted DNA contains sequence diversity, then each recipient phage displays one variant of the template (parental) amino acid sequence encoded by the DNA, and the phage population (library) displays a vast number of different but related amino acid sequences.

Such techniques make it possible not only to screen a large number of potential binding molecules but make it practical to repeat the binding/elution cycles and to build secondary, biased libraries for screening analog-displaying packages that meet initial criteria.

It is well-known to those normally skilled in the art that it is possible to replace peptides with peptidomimetics. Peptidomimetics are generally preferable as therapeutic agents to peptides owing to their enhanced bioavailability and relative lack of attack from proteolytic enzymes. Techniques of molecular modeling may be used to design a peptidomimetics which mimic the structure of the SarR peptide disclosed herein. Accordingly, the present invention also provides peptidomimetics and other lead compounds which can be identified based on the data obtained from structural analysis of the SarR protein disclosed herein. A potential SarR analog is examined through the use of computer modeling using a docking program such as GRAM, DOCK, or AUTODOCK. This procedure can include computer fitting of potential SarR analogs. Computer programs can also be employed to estimate the attraction, repulsion, and steric hindrance of an analog to a potential binding site. Generally the tighter the fit (e.g., the lower the steric hindrance, and/or the greater the attractive force) the more potent the potential drug will be since these properties are consistent with a tighter binding constant. Furthermore, the more specificity in the design of a potential drug the more likely that the drug will not interfere with other properties of the sarA expression system. This will minimize potential side-effects due to unwanted interactions with other proteins.

Initially a potential SarR analog could be obtained by screening a random peptide library produced by a recombinant bacteriophage, for example, or a chemical library. A analog ligand selected in this manner could be then be systematically modified by computer modeling programs until one or more promising potential ligands are identified.

Such computer modeling allows the selection of a finite number of rational chemical modifications, as opposed to the countless number of essentially random chemical modifications that could be made, and of which any one might lead to a useful drug. Thus through the use of the three-dimensional structure disclosed herein and computer modeling, a large number of compounds is rapidly screened and a few likely candidates can be determined without the laborious synthesis of untold numbers of compounds.

Once a potential SarR analog is identified it can be either selected from a library of chemicals commercially available from most large chemical companies including Merck, GlaxoWelcome, Bristol Meyers Squib, Monsanto/Searle, Eli Lilly, Novartis and Pharmacia UpJohn, or alternatively the potential ligand is synthesized de novo. As mentioned above, the de novo synthesis of one or even a relatively small group of specific compounds is reasonable in the art of drug design.

In a further aspect, this invention provides methods of treating a bacterial infection by administering a pharmaceutical composition comprising a SarR analog, peptide, or peptidomimitic to inhibit the expression of sarA. The present invention also provides a method for prophylactic treatment of a mammal, in particular a human, in order to prevent a bacterial infection. Such treatment comprises administering a pharmaceutical preparation comprising a SarR analog, peptide, or peptidomimetic to the mammal. Preferably such treatment would be used when the patient is at risk of contracting or developing a bacterial infection. Such a prophylactic treatment method may have particular benefit, for example, for treating patients prior to surgical operations.

Pharmaceutical compositions according to the present invention may comprise peptides and peptidomimetics of the present invention in association with a pharmaceutically acceptable carrier or excipient, adapted for use in human or veterinary medicine. The compositions may contain from 0.001-99% of the active material. Such compositions may be presented for use in conventional manner in admixture with one or more physiologically acceptable carriers of excipients. The pharmaceutical compositions according to the invention may also contain other active ingredients such as antimicrobial agents, or preservatives. The compositions may optionally further contain one or more other therapeutic agents which may, if desired, be a chemotherapeutic antiviral agent.

Pharmaceutically acceptable salts of the peptides of this invention may be formed conventionally by reaction with an appropriate acid. The additional salts so formed from addition by acid may be identified by hydrochloric, hydrobromic, phosphoric, acetic, fumaric, salicylic, citric, lactic, mandelic, tartaric, oxalic, methanesulfonic, and the like.

Thus, the peptides and peptidomimetics according to the present invention may be formulated for oral, buccal, parenteral, topical or rectal administration. In particular, these peptides and peptidomimetics may be formulated for injection or for infusion and may be presented in unit dose form in ampoules or in multidose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form for constitution with a suitable vehicle, e.g. sterile, pyrogen-free water, before use.

The present invention further provides a process for preparing a pharmaceutical composition which comprises bringing a peptide or peptidomimetic of the invention into association with a pharmaceutically acceptable excipient or carrier.

The dosage of the peptide or peptidomimetic used in the treatment will vary, depending on the seriousness of the disorder, the weight of the patient, the relative efficacy of the peptide and the judgment of the treating physician. Unit dosages may be administered more than once a day, e g., two or three times a day. Such therapy may extend for several weeks, in an intermittent or uninterrupted manner, until the patient's symptoms are eliminated.

The present invention also provides pharmaceutical compositions which comprise a pharmaceutically effective amount of the peptides of this invention, or pharmaceutically acceptable salts thereof, and, preferably, a pharmaceutically acceptable carrier or adjuvant. Therapeutic methods of this invention comprise the step of treating patients in a pharmaceutically acceptable manner with those peptides or compositions. Such compositions may be in the form of tablets, capsules, caplets, powders, granules, lozenges, suppositories, reconstitutable powders, or liquid preparations, such as oral or sterile parenteral solutions or suspensions.

In order to obtain consistency of administration, it is preferred that a composition of the invention is in the form of a unit dose. The unit dose presentation forms for oral administration may be tablets and capsules and may contain conventional expedients. For example binding agents, such as acacia, gelatin, sorbitol, or polyvinylpyrrolidone; fillers, such as lactose, sugar, maize-starch, calcium phosphate, sorbitol or glycine; tabletting lubricants such as magnesium stearate; disintegrants, such as starch, polyvinylpyrrolidone, sodium starch glycolate or microcrystalline cellulose; or pharmaceutically acceptable wetting agents such as sodium lauryl sulfate.

The solid oral compositions may be prepared by conventional methods of blending, filling, tabletting, or the like. Repeated blending operations may be used to distribute the active agent throughout those compositions employing large quantities of fillers. Such operations are, of course, conventional in the art. The tablets may be coated according to methods well-known in normal pharmaceutical practice, in particular with an enteric coating.

Oral liquid preparations may be in the form of emulsions, syrups, or elixirs, or may be presented as a dry product-for reconstitution with water or other suitable vehicle before use. Such liquid preparations may or may not contain conventional additives. For example suspending agents, such as sorbitol, syrup, methyl cellulose, gelatin, hydroxyethylcellulose, carboxymethylcellulose, aluminum stearate gel, or hydrogenated edible fats; emulsifying agents, such as sorbitan monooleate or acacia; non-aqueous vehicles (which may include edible oils), such as almond oil, fractionated coconut oil, oily esters selected from the group consisting of glycerine, propylene glycol, ethylene glycol, and ethyl alcohol; preservatives, for instance methyl para-hydroxybenzoate, ethyl para-hydroxybenzoate, n-propyl parahydroxybenzoate, or n-butyl parahydroxybenzoate or sorbic acid; and, if desired, conventional flavoring or coloring agents.

For parenteral administration, fluid unit dosage forms may be prepared by utilizing the peptide and a sterile vehicle, and, depending on the concentration employed, may be either suspended or dissolved in the vehicle. In preparing solutions, the peptides of this invention may be dissolved in water, whereas opiates used heretofore showed only marginal solubility in aqueous media or physiological fluids. Once in solution, the peptide may be injected and filter sterilized before filling a suitable vial or ampoule and subsequently sealing the carrier or storage package. Adjuvants, such as a local anaesthetic, a preservative or a buffering agent, may be dissolved in the vehicle prior to use. Stability of the pharmaceutical composition may be enhanced by freezing the composition after filling the vial and removing the water under vacuum, e.g., freeze drying the composition. Parenteral suspensions may be prepared in substantially the same manner, except that the peptide should be suspended in the vehicle rather than being dissolved. A surfactant or wetting solution may be advantageously included in the composition to facilitate uniform distribution of the peptide.

Experimental Materials, Methods and Results

Bacterial Strains and Growth Conditions. As way of example, certain bacterial strains and plasmids used herein are listed in Table 1 as shown below.

TABLE 1

| Strains or plasmid | References | Comments |
|---|---|---|
| S. aureus | | |
| RN4220 | (32) | A mutant of 8325-4 that accepts DNA |
| RN6390 | (32) | Laboratory strain that maintains its hemolytic pattern when propagated on sheep erythrocyte agar (parental strain) |
| RN6911 | (34) | An agr mutant of RN6390 with an agr::tetM mutation |
| ALC488 | (9) | A sarA mutant with a sarA::ermC mutation |
| ALC1713 | this study | A sarR mutant of RN6390 with a sarR::ermC mutation |
| Cowan I | (17) | A laboratory strain |
| DB | (10) | A clinical blood isolate previously used in adhesion and endocarditis studies |
| Newman | (29) | A laboratory strain |
| S. epidermidis | | A strain from the collection at the Utrecht University Hospital |
| S. haemolyticus | | A strain from the collection at the Utrecht University Hospital |
| S. saprophyticus | | A strain from the collection at the Utrecht University Hospital |
| E. coli | | |
| XL-1 blue | (26) | A host strain for cloning |
| DH5α | (26) | A host strain for cloning |
| Plasmids | | |
| pCR2.1 | Invitrogen | E. coli cloning vector for direct cloning of PCR products |
| pBluescript | Stratagene | E. coli cloning vector |
| pUC18 | (26) | E. coli cloning vector |
| pACYC177 | New England BioLabs | E. coli cloning vector |
| pCL52.1 | (24) | A temperature sensitive E. coli/S. aureus shuttle vector |
| pET11b | Novagen | Expression vector for E. coli |
| pALC926 | this study | pUC18 containing a 49-bp fragment upstream of the P2 promoter of the sarA locus |
| pALC1357 | this study | pET11b containing the 345-bp sarR gene at the NdcI/BamHI site |
| pALC1361 | this study | pACYC177 with ~4 kb ClaI fragment containing the sarR region of RN6390 |
| pALC1627 | this study | pBluescript with a 2.5 kb EcoRI/ClaI fragment containing the sarR gene subcloned from pALC1361 |
| pALC1687 | this study | pBluescript with a 290-bp deletion of the sarR gene in pALC1627 |
| pALC1696 | this study | pCL52.1 with a 290-bp sarR deletion replaced by the ermC gene at the EcoRV/SalI site |

Phage Φ11 was used as the transducing phage for S. aureus strains. S. aureus strain RN4220, a restriction-deficient derivative of strain 8325-4 (47), was used as the initial recipient for the transformation of plasmid construct by electroporation, following the protocol of Schenk and Laddaga (58).

S. aureus cells were grown at 37° C. with aeration in CYGP or 03GL broth (47,48) or tryptic soy broth supplemented with antibiotics when necessary. 03GL and NYE agar (58) containing antibiotics were routinely used for the selection of S. aureus transformants. Luria-Bertani medium was used for growing Escherichia coli. Antibiotics were used at the following concentrations: erythromycin, 5 μg/ml; tetracycline, 5 μg/ml and chloramphenicol, 10 μg/ml for S. aureus; and ampicillin, 50 μg/ml; chloramphenicol, 30 μg/ml; erythromycin, 200 μg/ml and spectinomycin, 75 μg/ml for E. coli.

Cloning of the sarR gene and construction of the sarR mutant. The SarR protein was partially purified from crude cell lysate by passing the lysate over a DNA-specific column containing a 49-bp DNA fragment (nt 71-119) covalently linked to Sepharose (18). The first 14 residues of the SarR protein in the amino-terminus were determined by microsequencing at the Core Facility at our institution. A blast search of the S. aureus genome data bank at TIGR revealed a partial ORF of 47 amino acids. Using these data, a 141-bp fragment with two degenerate oligos was amplified by PCR.

(5'-ATG T/A C/G A/T AAAAT T/C AA T/C GATAT T/C AA T/C GATTTT-3') (SEQ. ID NO: 4);

(5'-ATT T/A G/C A/T T/C TC T/A G/C A/T A/T C GIT T/C AA A/G AT A/G TG A/G TT T/C AA-3') (SEQ. ID NO. 5) The PCR fragment was cloned into the vector pCR2.1 (Invitrogen). Southern hybridization of enzyme-restricted chromosomal DNA of the parental strain RN6390 with a radiolabeled 141-bp DNA probe revealed a single ~4 kb Cla I-digested hybridizing fragment. To clone this fragment, ClaI-digested chromosomal DNA in the range of 3-5 kb was resolved in an agarose gel, excised, purified and ligated to the ClaI site of pACYC177 in E. coli DH5α. Positive-reacting clones were identified, all containing the ~4 kb ClaI fragment. One of these clones was sequenced, revealing a 345-bp ORF with identity to the partial 47 amino acid sequence of sarR as predicted from the S. aureus genome.

Deletion and insertion mutagenesis was performed with the Stratagene Quick Change kit to introduce a deletion and a mutation concomitantly into the sarR gene. In brief, the ~4 kb ClaI DNA fragment containing the sarR gene in recombinant pACYC 177 was cloned into pBluescript to serve as a template for mutagenesis. The following oligonucleotide

[SEQ ID. NOs: 6 and 7]
(5'-²²GCATGAAAAAGATATCGGGCATTT⁴⁵⁻³³⁸GTGAGTCTAACGATATCTCATCTAAA³⁶³-3')
           T    T                              A and its complement were used to construct a deletion and to introduce an exogenous EcoRV restriction site into the sarR gene (restriction site underlined, with the native nucleotides displayed below, intact sarR gene from nt 208-555). After amplification with the recombinant pBluescript template, the PCR product was digested with DpnI to remove methylated template DNA (i.e. pBluescript with the native sarR gene) and transformed into XL1-Blue cells to select for ampicillin-resistant colonies. Successful deletion and mutation in the resultant clones were confirmed by restriction analysis with EcoRV and finally verified by automated DNA sequencing. The ermC gene was then ligated to the EcoRV site of the mutated construct. The fragment containing an ermC replacement of the sarR gene was cloned into the temperature sensitive shuttle vector pCL52.1 (57) which was then transformed into RN4220 by electroporation (58) followed by transduction into RN6390 with phage Φ11 as described (15). Transductants were selected at 30° C. on erythromycin and tetracycline-containing plates.

S. aureus RN6390 harboring the recombinant pCL52.1 was grown overnight at 30° C. in liquid medium in the presence of erythromycin, diluted 1:1000 in fresh media and propagated at 42° C., a non-permissive temperature for the replication of pCL52.1. This cycle was repeated four times and the cells replicate-plated onto O3GL plates containing erythromycin and erythromycin/tetracycline to select for tetracycline-sensitive but erythromycin-resistant colonies, representing mutants with double-crossovers. The mutations were confirmed by Southern hybridization with sarR and ermC probes.

Southern Blot Hybridization. Chromosomal DNA of assorted staphylococcal species was isolated from lysostaphin-treated cells as previously described (15), restriction-digested, resolved in agarose gels and transferred onto a Hybond N+ membrane (Amersham, Arlington Heights, Ill.). Hybridization was performed under high stringency conditions with $^{32}$P-labeled DNA probes as described (15). The blots were subsequently washed and autoradiographed.

Purification of proteins. The intact 345 bp sarR gene was amplified by PCR using RN6390 chromosomal DNA as the template and primers containing flanking restriction sites (NdeI and BamHI) to facilitate cloning into expression vector pET11b (Novagen). The recombinant plasmid containing the sarR gene was transformed to E. coli BL21(DE3) pLysS. Enhanced expression of SarR was induced by adding IPTG (isopropyl-1-thio-b-D-galactopyranoside) to a 2 L growing culture (37° C.) at an $OD_{650}$ of 0.7. After 4 hrs of additional growth, cells were harvested, resuspended in buffer (25 mM Tris-Cl, 1 mM EDTA, pH 8.0, 100 mM NaCl, 10% sucrose and 1 mM DTT), flash-frozen and thawed twice and clarified by centrifugation at 4° C. (45,000 rpm for 1 h). After precipitation with 80% ammonium sulfate, the pellets were dissolved in buffer A (10 mM Tris-Cl, pH 7.5, 1 mM EDTA, 100 mM NaCl, 10% glycerol, and 1 mM DTT), dialyzed against buffer A, applied to a Resource-Q column in an AKTA purifier (Pharmacia, Piscataway, N.J.). The flow-through was re-applied to a Resource-S column and eluted with a NaCl gradient. The fractions were analyzed in a 12% SDS-polyacrylamide gel. Fractions containing the putative SarR protein were pooled, dialyzed against buffer A with 40% glycerol and stored at −80° C. The authenticity of the SarR protein was confirmed by determining the N-15 residues with microsequencing. The concentration of the purified protein was determined with the Bio-Rad Protein Assay solution (Bio-Rad Laboratories, Richmond, Calif.), using BSA as the standard.

Production of anti-sarR monoclonal antibodies. Purified SarR protein was used to immunize two BALB/c×SJL/J (F1 cross) mice (100 μg each) to obtain monoclonal antibodies as described (32). The titers of the immune sera were determined by an ELISA in which diluted sera were added to microtiter wells precoated with SarR (5 μg/ml) as described by Jones et al. (32). After splenic fusion, antibodies from limited dilutions were screened by an ELISA with immobilized SarR protein. Monoclonal antibodies were then purified from culture supernatants with a protein A-agarose column as described (32).

RNA isolation and Northern analysis. Overnight cultures of S. aureus were diluted 1:50 in CYGP broth with appropriate antibiotics and grown to mid-log ($OD_{650}$=0.7 with an 18 mm borosilicate glass tube), late-log ($OD_{650}$=1.1) and postexponential phases ($OD_{650}$=1.7). The cells were pelleted and processed with 1 ml of Trizol (Gibco-BRL, Gaithersburg, Md.) in combination with 0.1 mm diameter sirconia-silica beads in a Fast Prep reciprocating shaker (BIO101, San Diego, Calif.) as described (12). Ten micrograms of total cellular RNA from each sample was electrophoresed through a 1.5% agarose-0.66M formaldehyde gel in MOPS running buffer (20 mM MOPS, 10 mM sodium acetate, 2 mM EDTA, pH 7.2). RNA was transferred onto Hybond N+ membranes (Amersham) under mild alkaline conditions by using a Turboblotter system (Schleicher and Schuell, Keene, N.H.) as described by the manufacturer. RNA was fixed to the membrane by baking at 80° C. for 1 hr. For detection of specific transcripts, gel purified DNA probes were radiolabeled with $^{32}$P-dCTP by using the random-primed method (Ready-To-Go labeling kit, Pharmacia) and hybridized under aqueous conditions at 65° C. The blots were subsequently washed and autoradiographed.

Promoter fusion analysis with the gfp$_{uvr}$ reporter gene. To confirm the effect of the sarR mutation on sarA promoter activities, sarA promoter fragments (P1, P2, P3 and combined P2-P3-P1) (39) were cloned into shuttle vector pALC1484, which is a derivative of pSK236 containing the recombinant gfp$_{uvr}$ gene. The gfp$_{uvr}$ gene was constructed by introducing a S65T mutation into gfp$_{uv}$ (Clontech, Palo Alto, Calif.), thereby facilitating a shift in the excitation maxima from 395 to 488 nm (26). The sarA promoter fragments were then cloned into pALC 1484, upstream of the gfp$_{uvr}$ reporter gene. After sequence confirmation, the recombinant pALC1484s were then electroporated into RN4220 and transduced into S. aureus strains RN6390 and its isogenic sarR mutant (15).

The activities of sarA promoter fragments linked to the gfp$_{uvr}$ reporter gene in RN6390 and its isogenic sarR mutant were assayed by flow cytometry. Bacterial cell suspensions obtained at different parts of the growth cycle were analyzed in a FACScan (Becton Dickinson, Franklin Lakes, N.J.). After filtering bacterial samples through a 5 mμ filter to remove large aggregates, bacteria were detected by side scatter as described by Russo-Marie et al. (56). Fluorescence and side scatter data were collected with logarithmic amplifiers. The fluorescence data were reported in fluorescence units as specified by the instrument (FACScan).

To obtain more quantitative fluorescence data, each of the above gfp$_{uvr}$ reporter constructs was diluted 1:100 from overnight cultures into fresh CYGP medium and, beginning at the second hour, sampled hourly (200 µl) for 10 h to encompass the growth cycle from log to stationary phases. The samples were analyzed for total fluorescence and optical densities (605 nm) in microtiter wells in a multi-purpose fluorescence spectrophotometer (FL600, BioTek Instrument, Winooski, Vt.). The fluorescence units and optical densities were given as reported by the instrument. The background was ~200-300 fluorescence units, with variations of less than 100 units between duplicate samples.

Cell extracts preparation and Western analysis. Cell-free extracts from midlog, latelog and early stationary phases (representing OD$_{650}$ of 0.7, 1.1 and 1.7, respectively, in an 18 mm borosilicate tube) were prepared from RN6390, the isogenic sarR mutant and other staphylococcal strains. Cells were grown in CYGP broth (50 ml) supplemented with the appropriate antibiotics. After pelleting, the cells were resuspended in 0.5 ml of TEG buffer (25 mM Tris-HCl, 5 mM EGTA; pH 8.0) and cell extracts were prepared from lysostaphin-treated cells as described by Mahmood and Khan (37).

Equivalent amounts of cellular proteins were separated in 12% sodium dodecyl sulfate (SDS) polyacrylamide gels and transferred onto nitrocellulose membranes as described (61). The blots were incubated at RT with 1:1000 or 1:2000 dilution of anti-SarR or anti-SarA monoclonal antibodies for 3 h followed by another hour of incubation with a 1:10,000 dilution of goat anti-mouse alkaline phosphatase conjugate (Jackson ImmunoResearch, West Grove, Pa.). Immunoreactive bands were detected as described by Blake et al. (3). SeaBlue prestained protein standards (Novex, San Diego, Calif.) were used for molecular weight estimations.

Gel shift analysis and DNaseI footprinting. Gel shift assays were performed to determine the interaction of purified SarR with sarA promoter fragments. DNA fragments were end-labeled with –$^{32}$P ATP by using polynucleotide kinase. Labeled DNA fragments were incubated at RT for 20 min with the indicated amounts of purified protein in 25 µl of binding buffer (25 mM Tris-HCl, pH 7.5, 0.1 mM EDTA, 75 mM NaCl, 1 mM DTT, 5% glycerol) containing 0.5 µg of calf thymus DNA. The reaction mixtures were analyzed by nondenaturing polyacrylamide gel electrophoresis as described (19). The band shifts were detected by exposing dried gels to film.

Footprinting assays with linear DNA template and DNase I were performed using a modification of the method previously described (21). A 49-bp fragment upstream of the sarA P2 promoter region (39) was cloned into the BamHI site of pUC18, yielding pALC926. A 109-bp EcoRI/HindIII fragment from pALC926 was gel-purified and end-labeled with –$^{32}$P. PCR fragments containing sarA P1 (nt 531-859 and nt 620-859) and P3 (nt 364-525) promoter regions were also used in footprinting reactions. To label these PCR products, only one of the primers was end-labeled with –$^{32}$P in the amplification reactions, yielding PCR products labeled at one end. For the assay, the binding reactions were carried cut in a 100 µl reaction volume containing 20 mM Tris-HCl (pH 8.0), 100 mM NaCl, 5 mM MgCl2, 1 mM CaCl2, 2 mM DTT, 10 µg of BSA, 0.4 µg of calf thymus DNA, template DNA and varying amounts of the SarR protein at RT for 30 min. DNaseI (0.02 unit) (Boehringer Mannheim, Indianapolis, Ind.) was added and allowed to incubate for 1 min at RT. The reaction mixtures were then extracted with phenol/chloroform. DNA was ethanol-precipitated, resuspended in loading buffer (98% formamide, 10 mM EDTA pH 8.0, 0.025% (w/v) xylene cyanol FF and 0.025% (w/v) bromophenol blue) and analyzed on a 6% denaturing polyacrylamide sequencing gel. The positions of the protected regions were identified by comparing the footprint with the A+G sequencing ladder of the same fragment (38).

Results: The sarA promoters are differentially expressed during the growth cycle, with P1 and P2 promoters being most active during the exponential phase and the P3 promoter activated postexponentially (39). Because of the complexity in promoter activation and the ensuing expression of sarA, the promoter region upstream of the sarA gene may serve as a binding site for one or more trans acting factors (2,39). Taking advantage of a P2 promoter sequence (2) that shares homology with a region upstream of the sar P1 promoter (FIG. 1A), a DNA-specific column, containing the 49-bp P2 promoter sequence, was used to partially purify a ~12 kDa protein with binding properties to sarA promoter fragments (39). In the schematic shown in FIG. 1A, the positions of the transcription starts (–146, –409 and –711 bp upstream of the translation start) for P1, P3 and P2 promoters are depicted according to published sequence (2). The P1, P3 and P2 transcripts have previously been designated as sarA P1, sarA P3 and sarA P2 transcripts. The 49-bp sequence outlined was used to construct a DNA-specific column as described (27). The relative positions of the sarA promoter fragments used in gel shift and footprinting studies are indicated (filled boxes) while the promoter fragments for the GFP transcriptional fusion assays are marked as empty boxes.

To further characterize this protein and to investigate its regulatory function, the sarR gene product was cloned and characterized using biochemical, immunological and genetic approaches.

Cloning and sequence analysis of the sarR gene. To clone the gene encoding SarR, we blotted the ~12 kDa protein onto a PVDF membrane for N-terminal sequencing. The first 14 amino acids were X(K)IND(I)NDLVNA(S/T)F, (SEQ. ID NO.: 8) with X being an unknown residue while those residues in parenthesis carried a putative assignment. In searching the Tiger databank of the partially released S. aureus genome, we obtained a partial ORF of 47 amino acids that corresponds to the N-terminal sequence of the ~12 kDa protein. By using two degenerate oligonucleotides of 30-nt each, a 141-bp fragment was amplified to probe a chromosomal digest of S. aureus strain RN6390, thus allowing identification of a ~4 kb ClaI hybridizing fragment. A plasmid DNA library containing ~3-5 kb ClaI fragments constructed in pACYC177 (26) was then screened with the 141-bp PCR-generated probe. A positive clone (pALC1361) yielding a ~4-kb insert at the ClaI site of pACYC177 vector was identified. In determining the sequence of the insert, and comparing the insert sequence with that of the 141-bp probe, the DNA sequence of the putative gene sarR was obtained (FIG. 1B) (GenBank accession #AF207701). The predicted SarR protein contains 115 amino acids, with a predominance of charged residues (34%) and a predicted molecular size of 13,689 daltons. The sarR gene has a putative Shine Dalgarno sequence (AGGAGTGG) (SEQ. ID NO: 9) lying 7-bp upstream of the translation start, with typical initiation (ATG) and termination codons (TAA). To ascertain the transcription start site and the putative promoter boxes, the 5'-end of the sarR transcript was mapped by primer extension, using an internal primer of the non-coding strand positioned near the N-terminus of the sarR coding region.

The transcription initiation site is located 88-bp upstream of the translation start, thereby allowing identification of the putative −10 and −35 promoter boxes as TAGAAT (SEQ ID NO: 10) and TTACCG (SEQ ID NO: 11), respectively (FIG. 1B).

In searching the GenBank for related proteins, the entire SarR protein shares sequence similarity with SarA (SEQ. ID NO. 3), with a high probability score of $1.8e^{-7}$ (FIG. 1C). There were also other SarR-homologs in the *S. aureus* database (University of Oklahoma *S. aureus* genome database). Like SarA, the SarR protein has a deduced basic pI (9.23). The sequence similarity between SarR and SarA is 51%, with 28% identity (FIG. 1C). In limiting the homology to specific regions, residues 52-75 of SarR were found to share homology with residues 54-77 of SarA. which, in turn, has a limited but regional sequence similarity to the DNA binding domain of VirF (residues 175-198), a transcription regulator of virulence gene expression in *Shigella flexneri* (18, 25).

Over-expression of SarR and production of monoclonal antibodies: To obtain a large amount of SarR, the sarR gene was cloned into pET11b and the gene product was over-expressed under an IPTG-inducible promoter in *E. coli* BL21. The expression, purification, and the purity of the SarR protein are shown in FIG. 2. Equivalent volumes of protein fractions during the purification process was applied to a 12% SDS-polyacrylamide gel. FIG. 2, Lane 1, whole cell lysate of *E. coli* containing pALC1357 (pET11b with the sarR gene); FIG. 2, lane 2, supernatant of the cell lysate after clarification by centrifugation; FIG. 2, lane 3, supernatant before 40% ammonium sulfate precipitation; FIG. 2, lane 4, pellet resulting from 40% ammonium sulfate precipitation; FIG. 2, lane 5, pellet from 80% ammonium sulfate precipitation; FIG. 2, lane 6, fall through of the redissolved 80% ammonium sulfate precipitant as applied to a MonoQ column (Pharmacia); FIG. 2, lane 7, fall through from the MonoS column (Pharmacia); FIG. 2, lane 8, NaCl elution from the MonoS column. N-terminal sequencing confirmed the identity of the purified SarR protein. The SarR protein was expressed primarily in the cytosolic fraction (FIG. 2, lane 2). After 80% ammonium sulfate precipitation (FIG. 2, lane 5), the redissolved proteins were dialyzed and applied to an anion exchange column (Resource-Q, Pharmacia), only to be found in the fall-through (FIG. 2, lane 6). The flow-though was then applied to a cation exchange column (Resource-S column, Pharmacia) and eluted with a salt gradient. Using this purification scheme, SarR was purified to near homogeneity (FIG. 2, lane 8). The authenticity of SarR was confirmed by N-terminal sequencing. The purified SarR was then used to immunize mice for the production of anti-SarR monoclonal antibodies. Three monoclonal antibodies, designated 2A7, 2C7, and 5E4 were obtained. Despite the similarity between SarR and SarA, cross-reactive studies indicated that anti-SarR monoclonal antibodies only reacted with SarR and not SarA on immunoblots.

The Existence of sarR in Other Staphylococcal Strains and Other Prokaryotes

PCR analysis was conducted to determine if the SarR gene is present in other *S. aureus* strains, other staphylococcal species and in other bacteria. This analysis demonstrates that the sarR gene is present in all strains of *S. aureus* as well as in *S. saprophyticus* and *S. haemolyticus*. Blast searches confirm this result.

Binding of SarR to SarA Promoter Fragments by Gel Shift and Footprinting Assays.

Figure 4A:
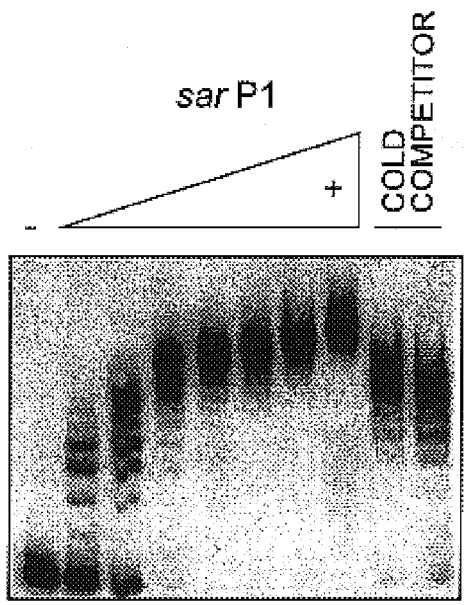
FIG. 4 shows gel shift assays of end-labeled $^{32}$P fragment of sarA P1 (nt 531-859) (2), P2 (nt 1-196) and P3 (nt 364-525) promoters.
Figure 4B:
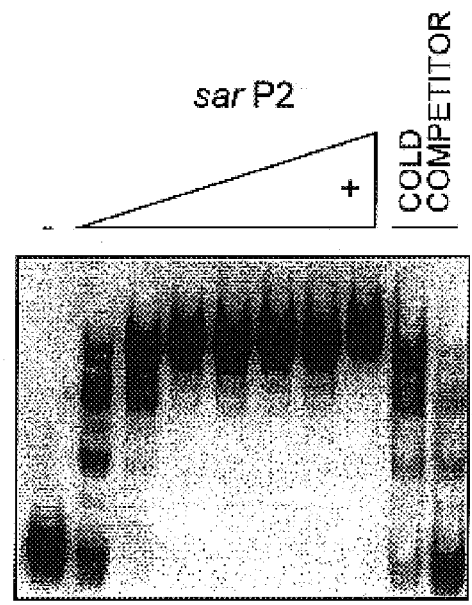
Figure 4C:
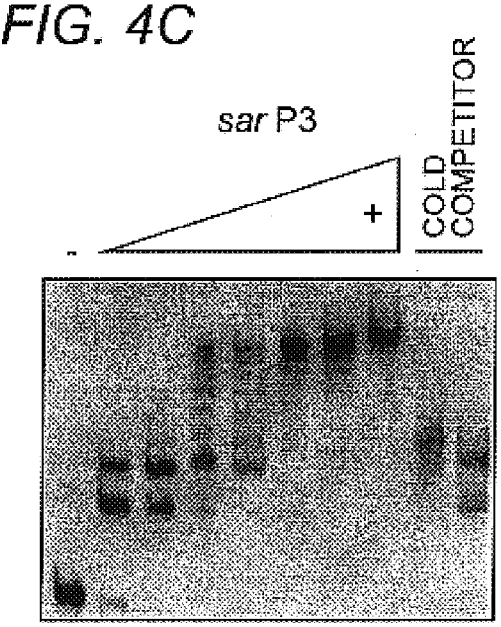

The interaction between SarR and various sarA promoter fragments was examined with gel shift and footprinting assays. Accordingly, purified recombinant SarR from *E. coli* was used in gel shift assays with assorted DNA fragments of the sarA promoter region including P2 (nt 1-196, P3 (nt 364-525), and P1 (nt 531-859). The mobility of the labeled DNA fragments became more hindered with increasing concentrations of SarR in gel shift assays (FIG. 4). In the assays, Increasing amounts (30, 60, 100, 150, 200, 250, 300 ng) of purified SarR were applied to the reaction mixtures. In competition assays, 50 and 100 fold excess of unlabeled DNA fragments were added. The unusual laddering pattern of the band shifts was observed with all three sarA promoter fragments. One plausible explanation is that each of the sarA promoter fragments may contain multiple binding sites. Alternatively, the binding of SarR in multimeric form to a common site or multiple sites within each of the sar promoter fragment is plausible. An analysis of the relative binding of SarR and SarA to the sarA P1 promoter indicates that the amount of SarA required to completely retard the mobility of 2-5 ng of radiolabeled sarA P1 fragment is 10 times more than that of SarR, thus demonstrating the higher avidity of SarR than SarA for the sarA P1 promoter fragment.

To determine the binding site of SarR and to verify the specificity of binding to the sarA promoter region, DNase I footprinting analysis was performed. To elucidate the SarR binding site, a 109-bp EcoRI-HindIII fragment derived from pUC18 containing the 49-bp sequence (39) was end-labeled at the EcoRI or HindIII sites separately and subjected to DNaseI footprinting with assorted concentrations of SarR. The sequence was deduced from G/A ladder reactions run in parallel following the standard method (26). The following amounts of SarR were applied to the sarA P2 and P1 reactions: 30, 60 and 100 ng, With sar P1', only lanes containing 30 and 60 ng of SarR protein were shown. The binding sites of SarR on the sarA P3 promoter was also mapped: 373 TTAC$\underline{TAAATTAAAAAAATTA}^{402}$ (SEA. ID NO. 12) (2). Analysis of the footprint of the plus strand (EcoRI site end-labeled) (FIG. 5A) disclosed the protected region (nt $^{81}\underline{TAAATTAA}$ TGTTATTTTTA$\underline{ATAATTTA}^{108}$) (SEQ ID. NO.13) (2) to be extremely A/T rich (96%), thus implying specific binding of SarR to this region but not to the more GC-rich polylinker region of pUC18, even when higher concentrations of SarR were used in the assay. A similar protection site was also found for the minus strand (HindIII site end-labeled). In analyzing the SarR protected region, the site was found to consist of a 7-8 sequence (TAAATTA$\underline{A}$ (SEQ ID. NO. 14), With the last base variable) conserved in both strands (e.g. $^{101}$ATAATTTA$^{108}$ (SEQ ID. NO. 15) being complement of TAAATTA$\underline{A}$) and throughout the sarA promoter region (39).

The binding of SarR to other sarA promoter regions was also determined. It has been shown that an inverted repeat region (nt 553-593) upstream of the sar P1 promoter may play a role in repressing sarA P1 transcription (39). Recognizing that SarR binds to a large P1 fragment in gel shift assays (FIG. 4), a footprinting analysis was performed with two different DNA fragments upstream of the sarA P1 promoter [329-bp (nt 531-859) and 240-bp (nt 620-859)(2)]. Using $^{32}$P end-labeled sense strand, the SarR-protected region on the 329-bp sarA P1 promoter fragment was found to comprise several regions including nt 551 to 553, 556 to 575, 582 to 603 ($^{586}$TAAATTA$\underline{T}^{593}$) (SEQ ID. NO. 16), 620 to 640 (FIG. 5B). In analyzing the smaller 240-bp P1 fragment, four additional protected regions, downstream of the above binding sites, were uncovered: nt 633 to 640, 643 to 667, 673 to 678, and 687 to 708 (FIG. 5C). Thus, the inverted repeat region (nt 553-593), which has previously been shown to play a putative role in repressing P1 transcription (39), is also part of the SarR binding sites. The SarR binding site on the sarA P3 promoter was also uncovered:

$^{373}$ $^{17}$TTAC<u>TAAATTAA</u>AAAAATTA$^{402}$ (SEQ I.D. NO. 17) (2). In comparing the broad binding sites protected by SarR, a common feature is their highly AT-rich nature. More remarkably, the 7-8 bp conserved sequence (TAAATTA<u>A</u>) (SEQ. ID NO:14) was included within the SarR binding sites in each of the sarA promoter fragments (P2, P1 and P3).

Figure 6A:
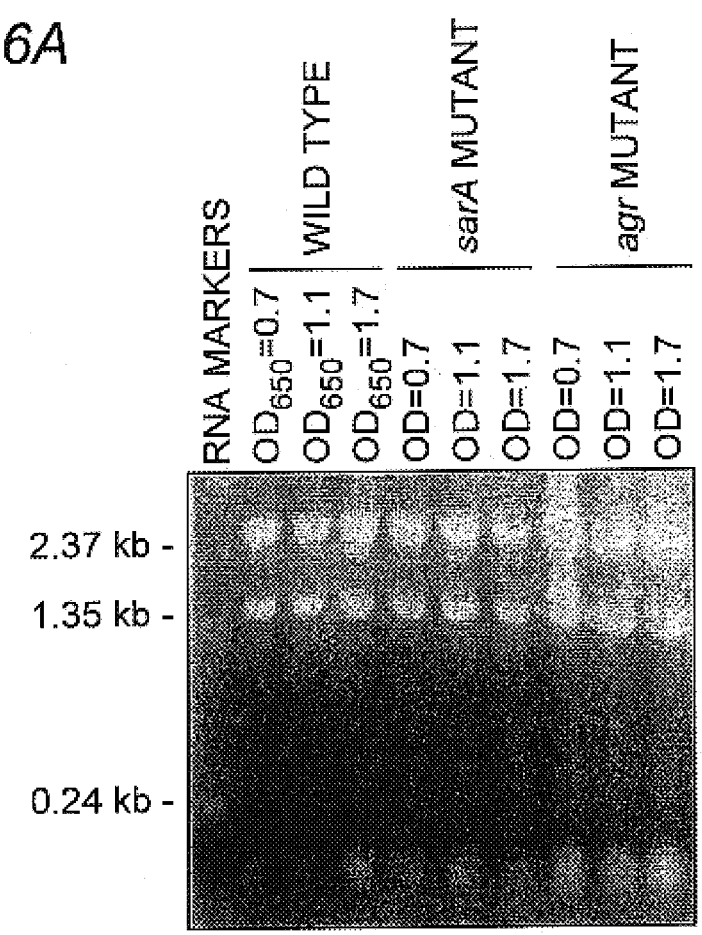
FIG. 6A illustrates Northern blots of the sarR transcript in RN6390 and its isogenic sar and agr mutants.

Expression of the sarR Gene in RN6390 and its Isogenic SarA and agr Mutants:

During the growth cycle, the major sarA gene product such as SarA partially mediates its effect by binding to the agr promoter to influence RNAII and RNAIII transcription. To ascertain if the sarR gene is modulated by sarA or agr (i.e. acting downstream of the sarA or agr regulatory cascade), sarR transcription in parental strain RN6390 and its isogenic agr and sarA mutants was assayed. To ensure that comparable amounts of total cellular RNA were applied to each lane, ribosomal RNA bands stained with ethidium bromide were compared among the lanes (FIG. 6A). Ten μg of total cellular RNA was applied to each lane. The sarR probe was a 345-bp fragment (nt 208-552). The $OD_{650nm}$ of 0.7, 1.1 and 1.7 represent mid log, late log and early stationary phase, respectively, as predicted from the growth cycle. As displayed in FIG. 6B, the transcription of sarR in RN6390 could be detected in mid log phase and was maximally expressed during the postexponential phase. Accounting for minor experimental variations, the observation that sarR transcription was not significantly altered in sarA and agr mutants indicated that sarA and agr did not regulate sarR as one would expect if these regulating loci lie downstream of sarR. This is consistent with the finding (described below) that a mutation in sarR affects sarA and agr transcriptions.

Figure 6B:
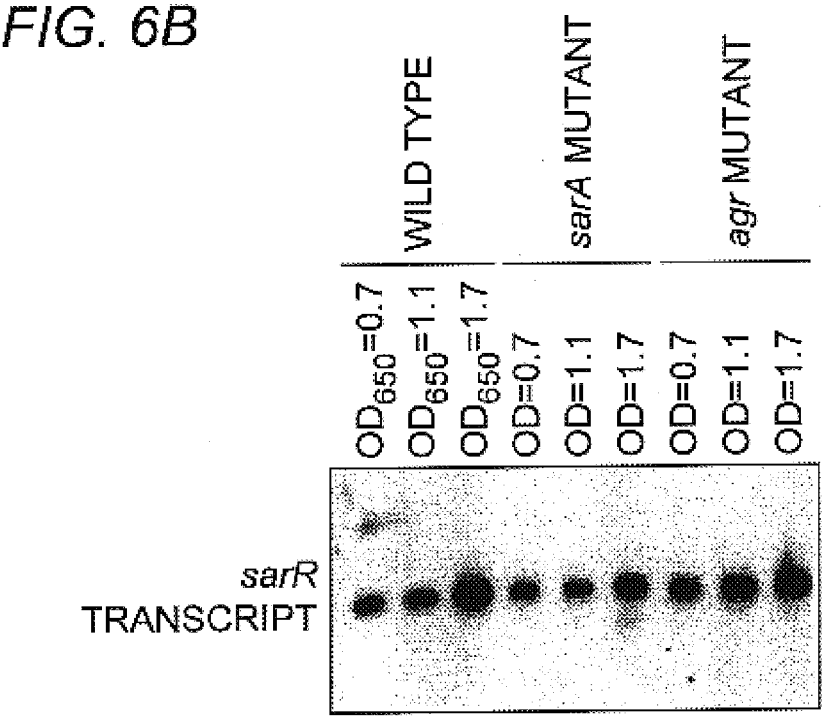
FIG. 6B illustrates ethidium bromide stain of an RNA gel prior to transfer to hybridization membrane.
Figure 6C:
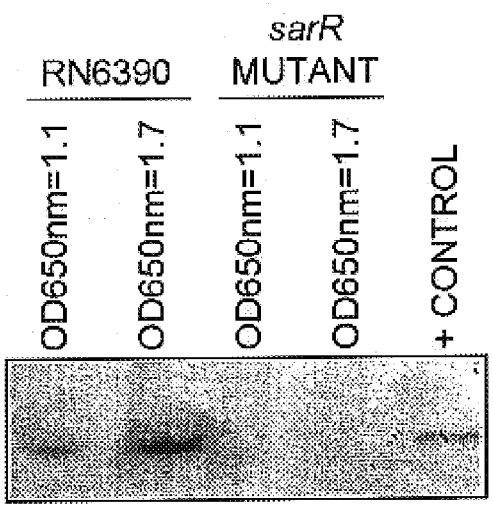
FIG. 6C illustrates the expression of sarR on an immunoblot probed with anti-sarR antibody 2C7.

The expression of the SarR protein during the growth cycle by immunoblots was also determined. Using anti-SarR monoclonal antibody 2C7 (1:1000 dilution), an immunoblot of cell-free extracts of RN6390 derived from cells grown to late-log ($OD_{650}$=1.1) and postexponential phases ($OD_{650}$=1.7) was probed. Employing ~25 μg of cellular proteins in each lane, it was found that the expression of SarR corresponds quite well with the pattern of sarR transcription, with SarR detectable at late-log phase, and maximal during the postexponential phase (FIG. 6C). In FIG. 6C, Each lane contains cell-free extracts (25 μg each) of RN6390 cells grown to late-log and early stationary phases. Cells at mid-log phase expressed little SarR; as expected, SarR was not detected in the sarR mutant ALC1713 (data not shown). The positive control lane contains 0.1 μg of purified SarR protein.

The expression of sarA in a sarR mutant: To demonstrate that the SarR protein likely modulates sarA expression by virtue of its binding to the sarA promoter region, a sarR deletion mutant was constructed by replacing the sarR gene with an ermC gene in strain RN6390. Northern analysis confirmed that the transcription of sarR was disrupted in sarR mutant ALC1713. To analyze the effect of sarR on individual sarA promoters, P2 (nt 1-180 plus 197-bp upstream), P3 (nt 364-525), P1 (nt 620-859) and the combined (or native) P2-P3-P1 promoters (nt 1-859 plus 197-bp upstream) (2, 39) upstream of the $gfp_{uvr}$ reporter gene were cloned in shuttle plasmid pALC 1484. Flow cytometry used to evaluate promoter activity, demonstrated that the sarA P1 and the combined P2-P3-P1 promoters were more active in the sarR mutant than the parental control. Mean fluorescence was 5.01±0.29 (log scale) in RN6390 vs 5.84±0.13 in sarR mutant and 5.49±0.21 in RN6390 vs 8.44±0.24 in the mutant, for P1 and combined promoters, respectively, during the postexponential phase. However, the relative weakness of the sarA P3 and P2 promoters as compared with the P1 promoter (~20 to 30 fold less than of P1) (39), coupled with the relative stability of the GFP reporter, rendered flow cytometry less useful to record small variations in GFP expression during the growth cycle among 10,000 organisms gated for this experiment. Not surprisingly, we failed to detect differences in activation of the weaker sarA P3 and P2 promoters between the parent and the isogenic sarR mutant by flow cytometry (39). More specifically, the level of P2 and P3 activation as detected by flow cytometry was only slightly above backgrounds.

Figure 7A:
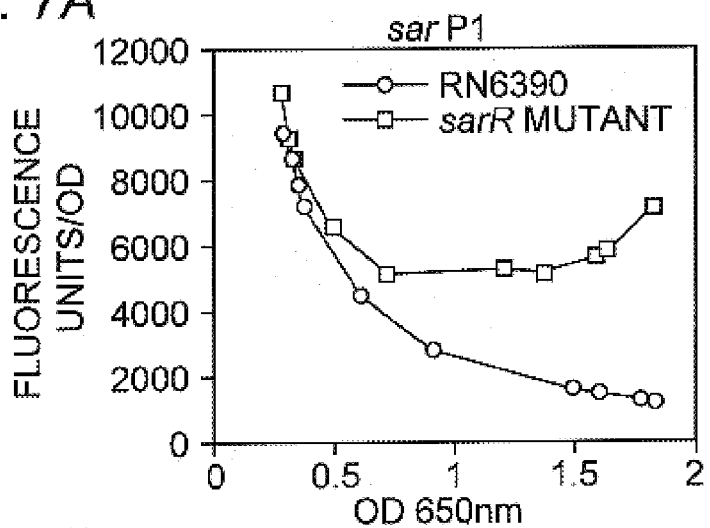
FIGS. 7A & B illustrate promoter activation of sarA P1 and combined P2-P3-P1 promoters fused to a gfp$_{uvr}$ reporter gene as evaluated in a fluorescence spectrophotometer (FL600, BioTek Instrument).
Figure 7B:
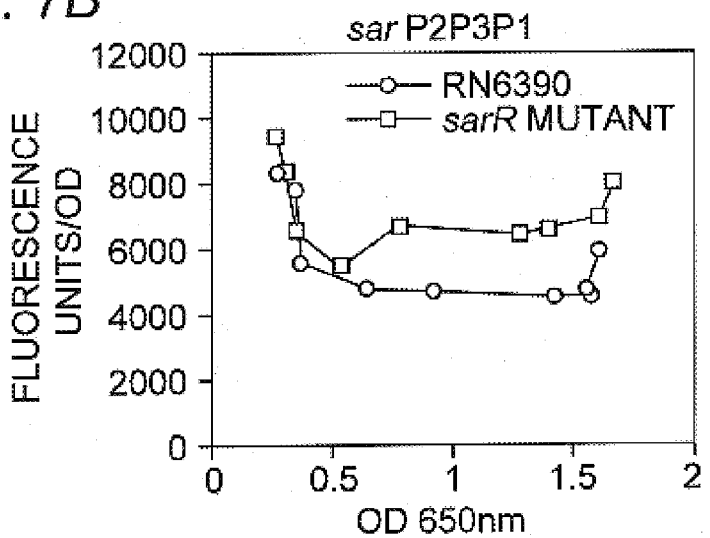
Figure 8A:
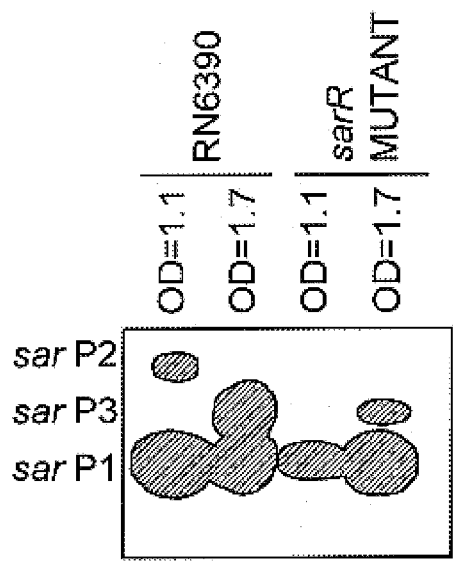
FIG. 8A illustrates sarA expression during mid-log and late-log phases and early stationary phases.

To obtain more quantitative fluorescence data for a larger number of bacterial cells, a multi-function fluorescence spectrophotometer in a microtiter format was used (FL600 from BioTek Instrument, Winooski, Vt.) to measure optical densities and total fluorescence of samples (200 μl) obtained serially during the growth cycle. To minimize the variation in fluorescence attributable to cell density, fluorescence per OD against optical densities was plotted over a 10 h period (extending from log to stationary phase). The data showed that the sarA P1-GFP fusion activity in the sarR mutant was higher than the parental strain (RN6390) throughout the growth cycle (FIG. 7A). FIG. 7A illustrates recombinant shuttle plasmid pALC1484 containing the sarA P1 promoter linked to $gfp_{uvr}$ (excitation maxima 488 nm) in strain RN6390 (μ) and its isogenic sarR mutant ALC1713. A negative control (RN6390 containing only pALC1484 without any promoter fragment) did not display any significant background fluorescence (~300 fluorescence units as the background, data not shown). Cells were obtained hourly (200 μl each in duplicate) during the growth cycle (from the $2^{nd}$ to the $10^{th}$ h after an initial dilution of 1:100 in fresh medium) to obtain fluorescence and optical densities (OD) in the same instrument. The data were presented as the average of reported fluorescence per OD in triplicate samples plotted against the mean of the optical densities. The error bar was too small to be discerned, typically less than 100 fluorescence units. This experiment has been repeated at least thrice. One representative experiment was shown. The early decline in fluorescence for both strains was likely to be attributed to the carryover effect of the GFP from the overnight inoculum. Following the decline, the highest level of GFP fusion in the mutant occurred late in the stationary phase (at ~7-10 h after initial culture dilution) (FIG. 7A), at a time when the sarR transcript level and the expression of SarR in the parent were highest (FIGS. 6B and 6C). The level of GFP fusion for the sarA P1 promoter in the parental strain declined after the initial dilution, but higher than the background (background fluorescence ~300 units), during the growth cycle. This finding is attributable to a steady decrease in P1 promoter activation (per bacterial cell) in the parental strain as the cell cycle progressed. Additionally, a lack of contribution from upstream promoters (i.e. P3 and P2) to modulate P1 activity in this promoter fragment may conceivably play a role. Similar studies were also conducted for the combined or native sarA P2-P3-P1 promoter linked to the $gfp_{uvr}$ reporter. In this instance, the combined promoter activity in the sarR mutant was also higher than that of the parent. FIG. 7B illustrates a plot similar to FIG. 7A except that the combined sarA P2-P3-P1 promoter fragment was used in place of the P1 promoter in the recombinant pALC1484 containing the $gfp_{uvr}$ reporter gene. Similar assays were also performed with the individual sar P2 and P3 promoters linked to the gfp$_{uvr}$ reporter in the isogenic pair, but failed to detect any differences in GFP$_{uvr}$ expression between the parental strain and the sarR mutant. However, the level of fluorescence associated with individual P2 and P3 promoters was very low and only slightly above backgrounds. As with the P1 promoter, the level of activity for the combined promoter decreased after initial culture dilution for both strains and then increased during the postexponential phase. Of interest, the increase in combined promoter activity with growth in the parental strain suggests that the sequence element upstream of P1 may have contributed to the overall increase in combined promoter activity during the postexponential phase. However, no differences in fluorescence for the P2 or the P3 promoter GFP fusions between the sarR mutant and its isogenic parent were detected. Notably, the fluorescence of the P2 and P3 promoters was only slightly above background. Thus, this shows that the fluorescent assays may not be sensitive enough to detect subtle differences in P2 and P3 promoter activities. To demonstrate that an intact sarR gene has a negative impact on the expression of SarA, the major sar regulatory molecule, cell-free extracts of the isogenic sarR strains during various stages of the growth cycle were obtained. Using cell extracts (25 μg of proteins each) of the sarR mutant obtained at different phases of the growth cycle, an immunoblot with anti-SarA monoclonal antibody 1D1 (20) was probed. As shown in FIG. 8A, the sarR mutant expressed higher levels of SarA protein than the isogenic parent at optical densities representing mid-log, late-log and stationary phases. FIG. 8A shows an immunoblot of the cell extracts (5 μg of protein each) of RN6390 and the sarR mutant (harvested at midlog, late-log and stationary phase) probed with anti-SarA monoclonal antibody 1D1 at 1:2000 dilution. The positive control lane contains 0.5 μg of purified SarA. Similar results were obtained with 25 μg of protein per lane. Notably, in both the parental and the mutant strains, SarA expression was maximal during the late-log phase and tapered toward the stationary phase. This shows that the reduction in SarA expression in the parental strain during the stationary phase is explained in part by increased proteolytic activity and hence processing of SarA in stationary cells (39, 51). Additional immunoblots with increased amounts of cell extracts (at 25 μg each) from mid-log, late-log and stationary phases also confirmed higher expression of sarA in the sarR mutant as compared to the parental strain. Taken together, these data demonstrate that SarR is a DNA binding protein that binds to the sarA promoter to down-regulate sarA expression.

Figure 8B:
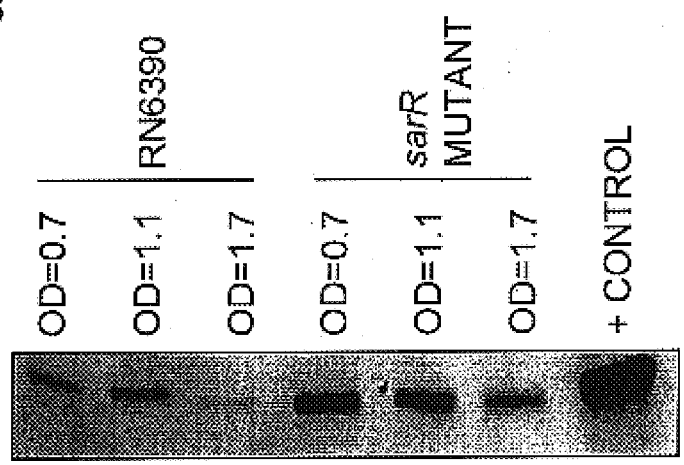
FIGS. 8B and 8C illustrate agrA (RNAII) transcription. Northern blots of the RNAII (agrA probe) transcript in RN6390 and the sarR mutant (10 µg of total RNA each) are shown. The agrA probe corresponds to nt 3830-4342 according to published sequence (23).
Figure 8C:
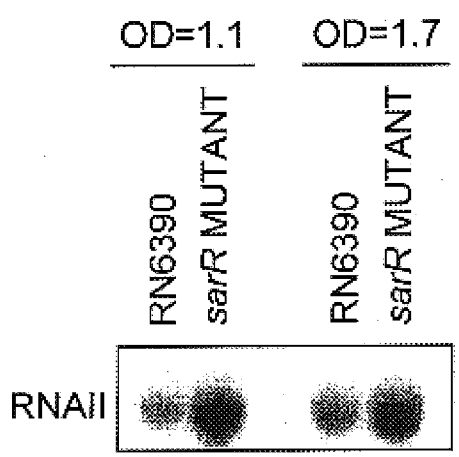

The level of SarA has been shown to correlate with the extent of agr activation (20). Northern analysis of sarR mutant ALC 1713 with an agrA (RNAII) probe confirmed a higher level of RNAII expression as compared with the parental control (FIG. 8B). Collectively, these data demonstrate that SarR down-regulates sarA expression, by binding to the sarA promoter to down-modulate sarA P1 transcription. The end result is the modulation of target genes (e.g. agr) downstream of the sarA regulatory cascade.

Protein expression, purification and crystallization: The intact 345-bp sarR gene was amplified by PCR using chromosomal DNA from *S. aureus* strain RN6390 as the template and primers containing flanking restriction sites (NdeI and BamHI) to facilitate cloning into an expression vector pMAL-c2 (BioLabs, Beverly, Mass.) modified by truncating 21 residues from the linker region that connects SarR and MBP. The recombinant plasmid containing the sarR gene was transformed to *E. coli* BL21(DE3)pLysS. Enhanced expression of sarR-MBP fusion was induced by adding IPTG (isopropyl-1-thio-b-D-galactopyranoside) to a 4 L growing culture (37° C.) at an OD$_{650}$ of 0.7. After 4 hrs of additional growth, cells were harvested, resuspended in buffer (50 mM Tris-HCl, 1 mM EDTA, pH 7.4, 300 mM NaCl, 5% glycerol and 1 mM DTT) and subjected to cell lysis through a continuous-flow French press. After a 20,000×g spin, the soluble fraction was loaded onto an amylose resin affinity column (10 ml) and the SarR-MBP fusion protein was eluted with 10 mM maltose. The protein was loaded onto a MonoQ (Pharmacia) ion-exchange column. After elution with a NaCl gradient (0.1 to 0.5 M) the fraction containing the protein was found to be homogeneous as determined by a Coomassie stained SDS-polyacrylamide gel. The concentration of the purified protein was determined with the Bio-Rad Protein Assay solution (Bio-Rad Laboratories, Richmond, Calif.), using BSA as the standard. The SarR-MBP fusion protein (15 mg/ml) was crystallized by vapor diffusion against a solution of 5 mM β-mercaptoethanol, 100 mM Na acetate, 100 mM NaCl, pH 4.6, and 18-22% PEG monomethyl ether 2000. For cryo-crystallography, crystals were soaked in steps of increasing glycerol concentration (5% each step every 30 min) and finally into 20% glycerol before flash-freezing.

Structure Determination and Refinement: Data were collected on a Rigaku R-axis IV system and beamline 5.0.2 at ALS. Data processing was performed with DENZO and SCALEPACK (50). The initial phases were obtained by a molecular replacement solution using the available MBP structure (53) and program AMoRe (45). 2Fo-Fc and Fo-Fc electron density maps were calculated by CNS (6). Map interpretation and model building were done using the program O (33). The map was improved by cycles of refinement using CNS with NCS constraints. A final refinement was performed with relaxed NCS-restraints as shown in Table 2 below. The final model contains residues 1-115 for molecule one of SarR, residues 1-115 for molecule two of sarR (FIG. 9B), residues 1-372 for both MBP molecules (FIG. 9A), two maltose molecules, and 190 water molecules. Stereochemical values are all within or better than the expected ranges for a 2.3 Å structure, as determined using PROCHECK (35).

TABLE 2

Summary of Crystallographic Analysis

Diffraction Data and MR statistics

| Crystal[a] | Resolution (Å) | R$_{merge}$[b] (%) | Reflections Measured/Unique | Completeness (%) | Solutions[e] | C.O.[e] | R[e] |
|---|---|---|---|---|---|---|---|
| Native I | 2.8 | 4.3 | 62396/20967 | 78.0 | 2 | 47.2 | 46.6 |
| Native II | 2.3 | 2.7 | 77545/37403 | 96.5 | | | |

TABLE 2-continued

Summary of Crystallographic Analysis

Refinement (Native II)

| Resolution (Å) | 20-4.58 | 3.65 | 3.19 | 2.90 | 2.69 | 2.53 | 2.40 | 2.30 | Total |
|---|---|---|---|---|---|---|---|---|---|
| No. reflections | 5696 | 5656 | 5512 | 5198 | 4788 | 4180 | 3454 | 2702 | 37186 |
| R-factor[c] | 15.27 | 20.16 | 29.30 | 33.14 | 36.95 | 38.04 | 38.86 | 41.56 | 23.24 |
| Free R-factor[d] | 21.94 | 24.45 | 32.45 | 38.65 | 39.36 | 38.79 | 35.91 | 38.02 | 28.22 | r.m.s. Deviations; Bonds, 0.009 Å; Angles, 1.4°

[a]Crystal spacegroup P1; a = 64.7 Å, b = 70.6 Å, c = 75.5 Å, $\alpha$ = 65.7°, $\beta$ = 67.2°, $\gamma$ = 69.6°, two sarR-MBP monomers/unit cell

[b]R-merge = $100 \times \sum_j |I_j - <I>| / \sum_j I_j$ with Bijovet pairs treated as equivalent

[c]R-factor = $\Sigma |F_{obs} \cdot F_{calc}|/\Sigma F_{obs}$ for all amplitudes with $F/\sigma(F) \geq 2$ measured in the indicated resolution bin

[d]Free R-factor was calculated with 5% of the data in each bin.

[e]Molecular replacement solutions, C.O. was correlation coefficients, and R, are defined in Amore (18)

Figure 9A:
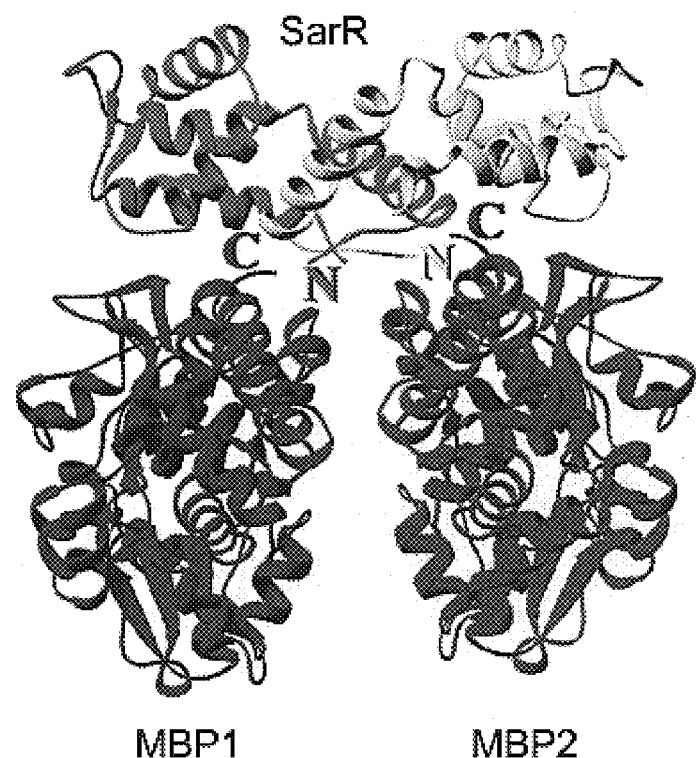
FIG. 9A illustrates a ribbon (8) diagram of the three-dimensional structure of the SarR-MBP fusion protein. The SarR dimer is at the top colored Green and Yellow for each monomer, respectively, two MBP molecules are at bottom colored Blue and Pink, respectively.
Figure 9B:
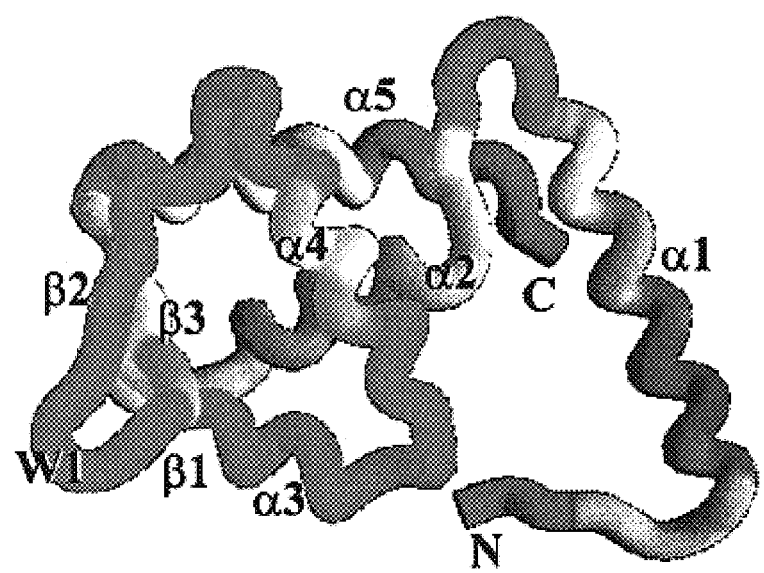
FIG. 9B illustrates a ribbon diagram of the three-dimensional structure of the SarR monomer. Starting from the N-terminus, α1 (6-24)→α2 (32-44) →β1 (47-50→α3 (residue 51-58)→α4 (63-74)→β2 (79-83) →β3 (90-96)→α5 (97-113). α2, β1, α3, α4, β2, and β3 are defined as a "winged helix motif". α3→α4 represent a helix-turn-helix-motif.

Overall Structure: The structure of SarR-MBP fusion protein shows that the SarR dimer is located at the top of the two individual MBP molecules, connected by two flexible loop regions between SarR and MBP. The positions of the MBP molecules suggest that they did not influence the structure of SarR dimer (FIG. 9A). The overall structure of the SarR monomer consists of five α helices, three short β strands, and several loops (FIG. 9B). The al helix extends out from the remaining molecule, forming a 'L' shaped like structure with a stretch formed from the N-terminal residues of the protein. The α2 helix follows a 7-residue loop from α1, and is almost perpendicular to α1 (85°). The three β strands, β1, β2, and β3, form an anti-parallel bundle, which is slightly twisted. α5 follows immediately after β3. Between β1 and β2 is a long flexible region (residues 51-79), which has poor electron density in the initial 2Fo-Fc and Fo-Fc maps, containing two helices, α3 (residue 51-56) and α4 (residue 63-75) respectively, and a short turn (residue 56-58). These three elements build up a typical helix-turn-helix structural module existing in DNA-binding proteins. Homology alignment of the SarR structure with all available structures shows that the SarR monomer is homologous to winged helix proteins (23), such as transcription regulatory protein mota fragment (PDB code 1bja) with Z score of 8.0, transcriptional repressor smtb activation domain (PDB code 1 smt) with Z score of 7.2. Compared to winged helix proteins, "W2" is replaced by a helix (α5) and the "W1" extends much further in the SarR monomer (FIG. 9B). The above data shows that SarR and its family of proteins are new members of the classic winged helix protein family.

Figure 10A:
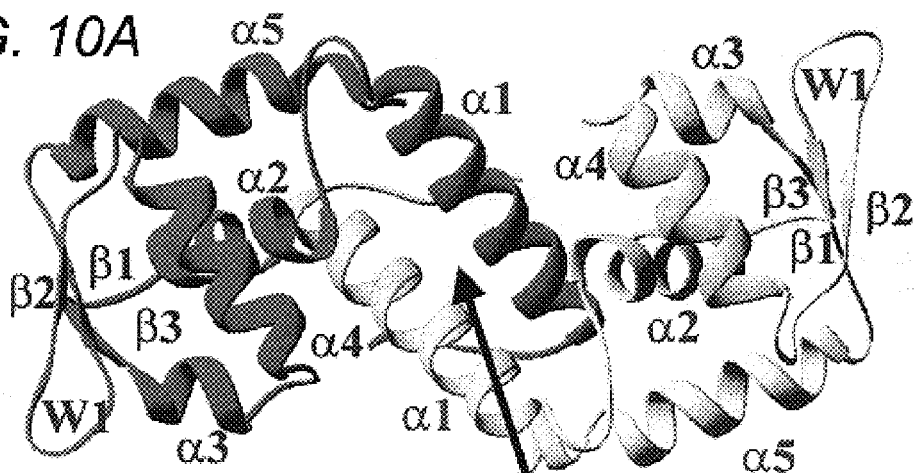
FIG. 10A illustrates one view of the structure of the SarR dimer. One SarR monomer is colored Green while the other is Yellow. This top view of the concave side along the dimer 2-fold axis of the SarR dimer, subdomain1 contains β1, α3, α4, β2, β3 (labeled blue) from one monomer, subdomain 2 contains β1, α3, α4, β2, β3 (also labeled blue) from the other, subdomain 3 contains α1, α2, α5 (labeled red) from both monomers.
Figure 10B:
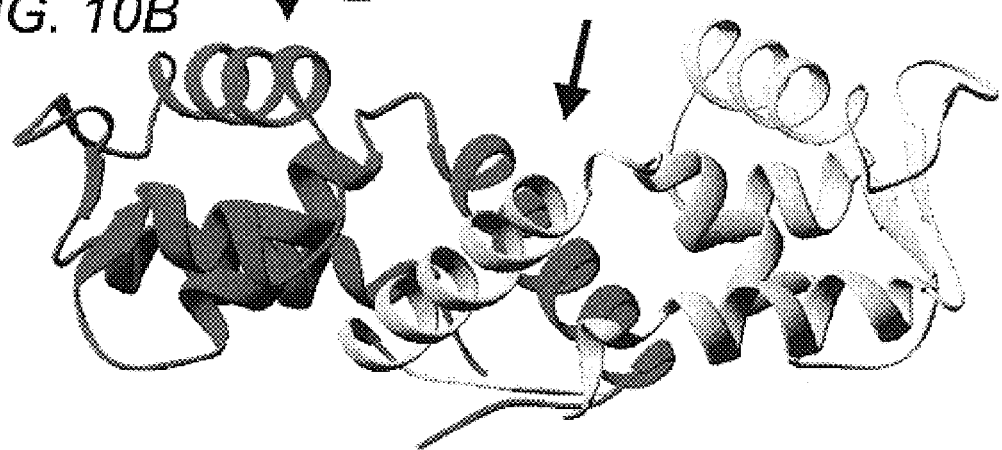
FIG. 10B illustrates a middle view perpendicular to the dimer 2-fold.
Figure 10C:
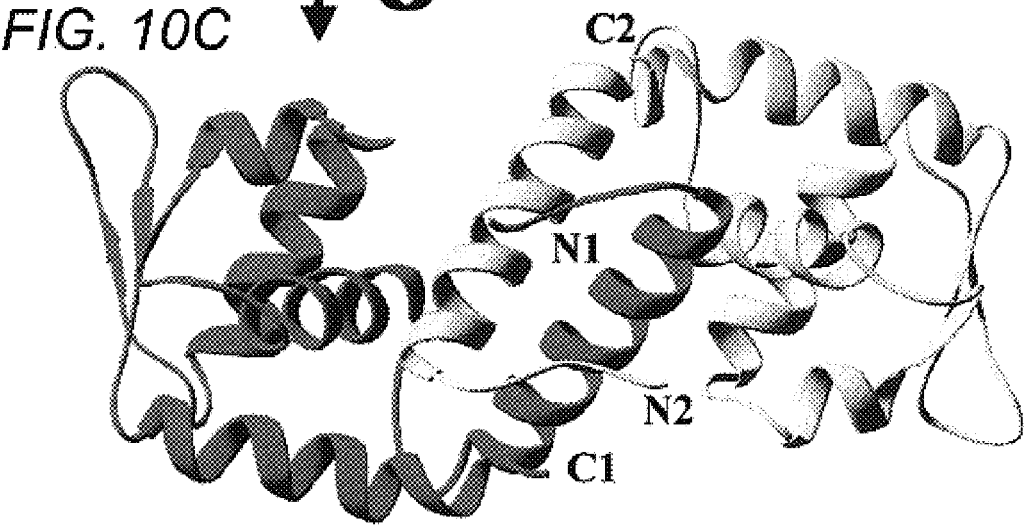
FIG. 10C illustrates a bottom view of the convex side of the SarR dimer. N1 and C1 are the N terminus and C terminus of molecule 1. N2 and C2 are termini of molecule two.

Two L-like structures of α1 and the stretch of the N-termini come together forming a dimer that has an elongated, slightly bent structure with overall dimensions of 71 Å×37 Å×34Å (FIGS. 10A and 10B). The monomers are related to each other by a non-crystallographic local two-fold axis. On the concave side and middle of the SarR dimer, there is a canyon like structure with length of ~35 Å, a width of ~25 Å, and a depth of ~10 Å (FIGS. 10A and 10B). The canyon is formed by a part of α1, the loop that connects α1 and α2 and a part of α2 as its bed, and with α4 from both monomers acting as the two banks (FIGS. 10A and 10B). On the convex side, all four termini (C and N-termini of both molecules) form a flat platform with the N-terminus of one monomer adjacent to the C-terminus of the other. This feature suggests that SarS, a 250 residue protein homologous to SarA (23), functions as a heterodimer-like monomer since it contains two sections, highly similar to the SarR module, each 125 residues long (17). The entire dimer can be described as three individual subdomain structures (FIG. 10A). Three beta strands plus α3 and α4 from each molecule form subdomain 1 and subdomain 2, respectively. Those two subdomains were poorly defined in the initial electron density map, which also was reflected by their high temperature factors compared to the average (89 via 69 ) in the final model, and can be expected to have high mobility in the molecule in solution. Subdomain 3, consisting of the major alpha helices α1, α2, and α5 from both monomers, is relatively rigid due to restrains of hydrophobic interactions. These helices in subdomain 3 are arranged in such a manner that the entire subdomain looks like a twisted letter Z with the relatively flexible subdomain 1 and subdomain 2 covering its ends. The Z-shaped scaffold, a unique structural feature for SarA family, represents a new functional protein fold (FIGS. 2A and 2B).

Figure 11:
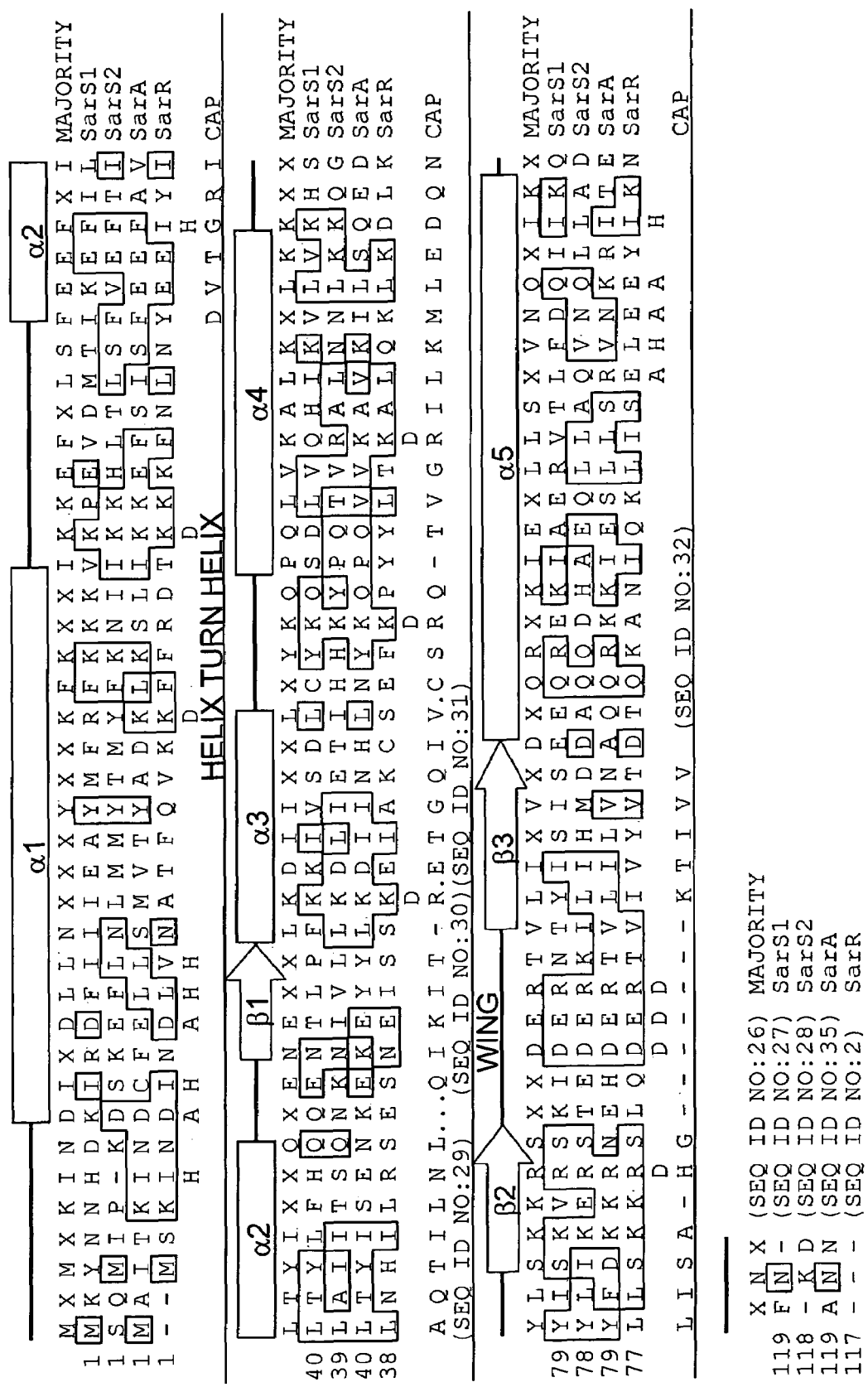
FIG. 11 illustrates a sequence alignment of Sar homologs from S. aureus. The sequences are presented in one-letter amino acid code. Numbers at the beginning of each line indicate amino acid positions relative to the start of each protein sequence. Helices are indicated by rectangles, β-sheets are indicated by arrows, and loops are indicated by a line. "H" marked with Green represents residues that take part in dimerization. "A" marked with Red represents residues that may compose of the activation motifs. "D" marked with Blue represents residues that is involved in the interactions of sarR with DNA. The sequence of DNA binding motif from CAP is also aligned to the Sar proteins. Dot means residue or residues omitted, dash means residue or residues missed in CAP. SarS2 starts at 1 (actual position on SarS is 126).

Dimerization Interfaces: Several lines of evidence suggest that, with the exception of SarS, the active form of the SarA family of proteins is a homodimer. First, there is strong evidence showing that SarA exists as homodimers in vitro as well as in vivo (60). Second, upon mixing partially unfolded (4M urea) full length SarR protein and SarR-MBP fusion, a heterodimer product containing one copy each of SarR and SarR-MBP fusion could be separated by gel-filtration chromatography. Third, crystals of SarR-MBP fusion protein were used to solve the SarR structure. The SarR protein exists as a dimer even in the MBP fusion form and indicating that the dimerization form is the active form existing in vivo. Fourth, based upon the homodimer SarR structure, the interactions between the two monomers are quite extensive, with most residues involved in hydrophobic interactions (FIGS. 9A and 11). Residues Leu10, Ile7, Ile 4 from one monomer and residues Phe20, Ile35, Leu 109 and Ile 113 from the other monomer form two hydrophobic cores. The dimer interface buries ~1,500 Å$^2$ of solvent-accessible surface area (1.4 Å probe, 25) per monomer. The hydrophobic feature of SarR dimerization, indicates that the dimer of SarR in the fusion protein is also the functional dimer in vivo. Furthermore, the L shape like structure of α1 and the stretch of the N-terminus of SarR physically block the dissociation of one monomer from its partner. This explains the need for extremely harsh conditions (e.g., 4M urea) in order to disrupt the dimerization of individual monomers. Fifth, deletion analysis showed that mutated sarA, with a 15-residue truncation at its N-terminus, exists as monomers in vitro (in solution or crystal packing forms). Finally, as shown by the sequence alignment of SarA, SarR, and SarS, most residues involved in the dimerization process are highly conserved (FIG. 11).

Figure 12A:
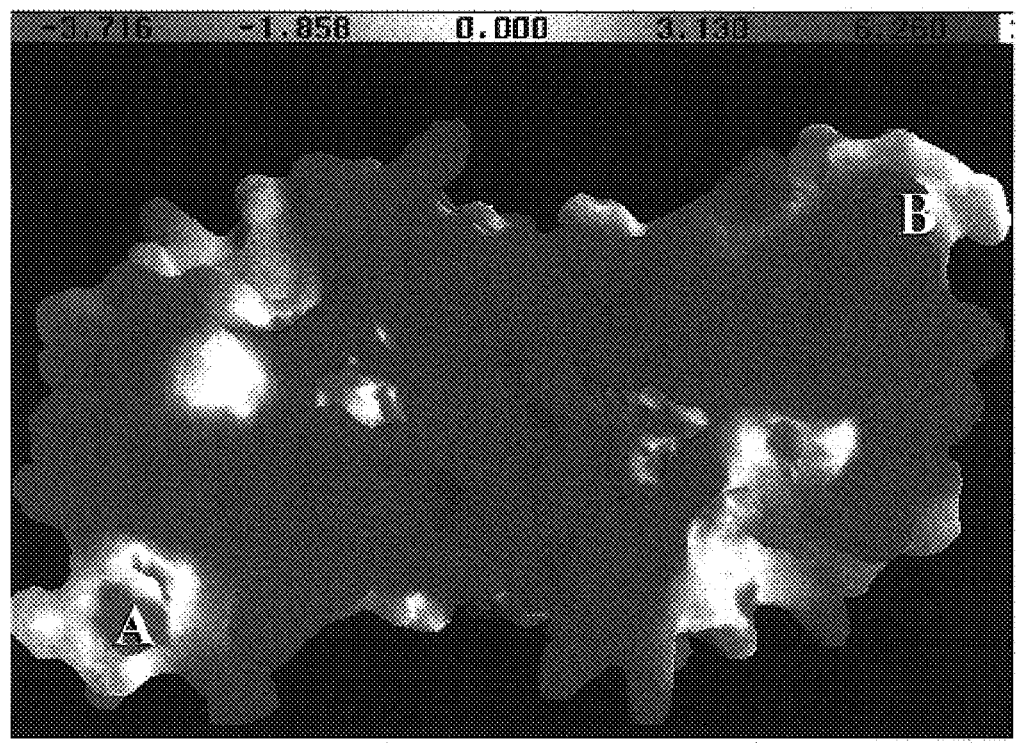
FIGS. 12A and 12B illustrate the electrostatic potential surface of the sarR dimer calculated by GRASP (46), with charge +1 for Lys and Arg, charge −1 for Glu and Asp, and charge zero for all other residues. The color bar from red to blue represents potential from negative to positive defined as in GRASP. The Blue represents positive charged potential, Red represents negative charged potential.

DNA Binding and Bending: The DNA binding domain of SarR is conserved in the SarA protein family. The binding domains include the helix turn helix motif and the wing of the SarR molecule. SarA and SarR proteins contain a high percentage of the residue Lys (39). Remarkably, most of the Lys residues are highly conserved between these two proteins (FIG. 1). It was predicted that most of these Lys residues are involved in DNA binding (39). Although the Lys residues are distributed throughout the entire primary sequence, in the 3D structure, most Lys residues and some Arg residues are located primarily on one surface of the SarR dimer (i.e., the concave side). The electrostatic potential on this surface of the SarR dimer, calculated by the Grasp program (46), revealed a positively charged track on this side (FIG. 12A). Additionally, the two winged helix motifs (domain 1 plus α2 from one monomer and domain 2 plus α2 from another monomer) are located on this side. Accordingly, this side is apparently the site for DNA binding.

Figure 13A:
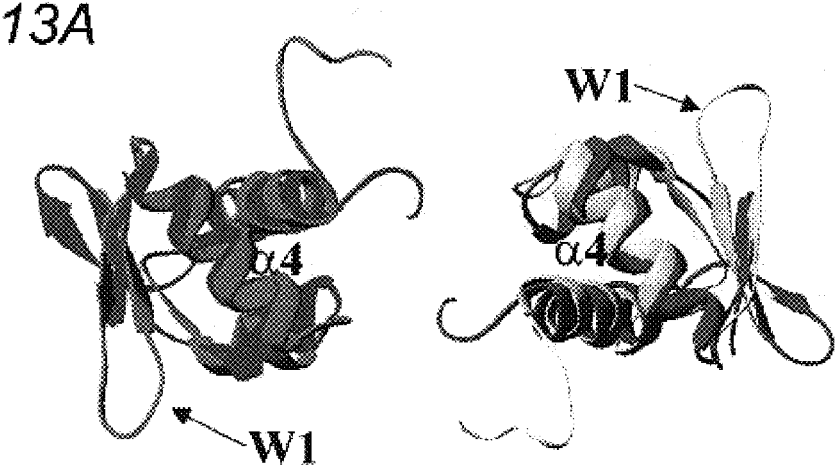
FIG. 13A illustrates the superposition of two "winged helix motifs" (subdomain 1 plus α2 from one monomer and subdomain 2 plus α2 from another monomer) of SarR dimer with the DNA binding domains of catabolite activating protein (CAP, PDB ID 1cgp); subdomains from SarR are marked Green and Yellow respectively; subdomains from CAP are marked Blue and Red; α4 and W1 interact with DNA at major grooves and minor grooves respectively.

Using the program Dali to search for proteins with a structure similar to SarR, every structure with a Z score higher than 4 was manually examined. It was determined that the spatial arrangement of the two SarR helix-turn-helix modules is quite similar to those in the catabolite activating protein (CAP) (33, PDB code 1cgp with Z score of 4.7). Superposing the SarR winged helix motif 1 and 2 with the corresponding domains from CAP dimer, the root mean square deviation (rmsd) of the cc-carbon backbone for motif 1 is 1.8 Å, and 2.1 Å for motif 2 (FIG. 13A). Interestingly, some of the residues involved in DNA binding and bending in the CAP dimer, which interact with the major grooves, are conserved in the SarR dimer and in other members of the Sar family (FIG. 1). For example, SarR charged residues that are predicted to interact with phosphate groups on the DNA backbone, are possibly Lys 52, Lys 56, Lys 71, and Arg 82. Lys 52 and Arg 82 are absolutely conserved in SarR and in the SarA family of proteins. Charged residues predicted to contact DNA bases are Lys 61 and Lys 67. Lys 61 is also absolutely conserved. Therefore, this shows that the SarR dimer and other SarA family members have similar protein-DNA interaction as the CAP dimer.

The interaction causes the DNA to bend at two points by ~90° (59). The longest direct distance for the CAP and SarR dimer surface is ~71 Å (FIG. 12), which can hold a stretch of bent DNA with ~27 base pair nucleotides that has length of ~92 Å for a normal B-form (59). This is consistent with the experimental DNA footprinting data, showing that ~29 nucleotides from the sarA promoter region were involved in binding to SarR (21). This predicted bending of the DNA when SarR binds to DNA, may reflect a regulatory mechanism for the SarA protein family in controlling target gene transcription.

Figure 13B:
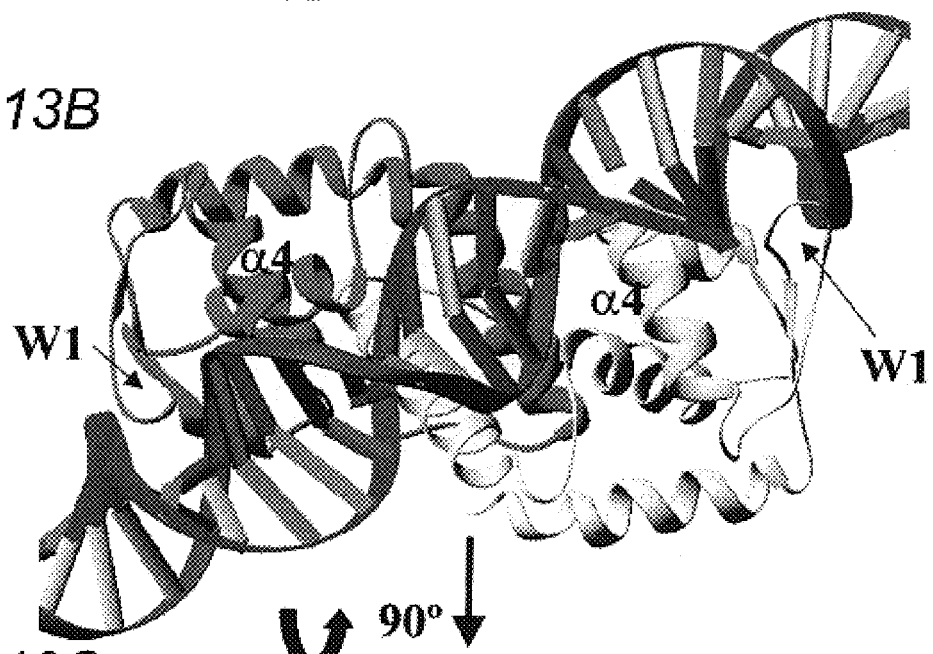
FIG. 13B illustrates the DNA binding model of SarR and DNA (similar orientation as FIG. 10A and FIG. 13A). The SarR dimer is superimposed to that of CAP. The DNA structure is from the CAP-DNA complex structure (PDB ID 1cgp). The helix-turn-helix-motif binds to the major groove while the wing region (W1) conformation is slightly adjusted to fit in the minor groove.
Figure 13C:
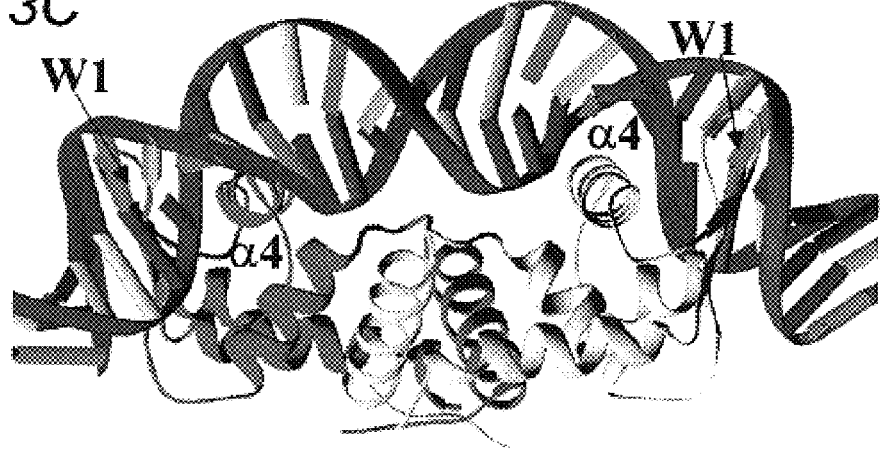
FIG. 13C illustrates a 90° orientation from view of FIG. 13B.

The SarR dimer was superimposed on the CAP-DNA complex to construct a model for a SarR-DNA complex (FIGS. 13B and C). This model suggests that in addition to interactions of the α4 helix with the DNA major groove, SarR makes contacts with the DNA minor groove. The loop region between β2 and β3 and part of the two beta strands (W1, a β-hairpin) should be quite flexible in the free SarR structure. Only slight adjustments of their conformations are required to position them to interact intensively with the minor groove of the DNA. Several residues that could be involved in the interactions are highly conserved: Asp 86, Glu 87, and Arg 88 with the side chain of Arg 88 interacting with the DNA phosphate backbone and the side chains of Asp 86 and Glu 87 interacting with bases (FIGS. 13B and C). This loop is too short in CAP and other winged helix proteins to have this minor groove binding function (23). One new member of one of the classes of winged helix proteins (RFX) does make DNA minor groove contacts, but in this case, the wing contacts the major groove and the helix contacted the minor groove (24). Therefore, the predicted SarR type of wing-minor groove interaction appears to be a unique feature of the SarA family of proteins establishing them as a third class of the winged helix family (23,24).

The two subdomains involved in the DNA binding and bending in CAP have different conformation at the absence of DNA, but are identical in the complex structure (23). The corresponding subdomains (1 and 2) in SarR are almost identical, but most of side chains are poorly defined. Those two subdomains should have high mobility in the absence of DNA just as these are in the CAP protein. The mobility can be reflected by their high temperature factors (FIG. 9A).

Regulation Mechanism: One class of transcription-activating proteins bears two structural motifs, namely a DNA binding and an activation domains (52). The SarR protein was initially defined as a transcriptional repressor protein that binds the sarA promoter region (39), thus leading to reduced transcription from the sarA P1 promoter. As stated previously, the sarA P1 promoter is the predominant promoter in the sarA regulatory system. Transcriptional fusion studies indicate that the sarA locus is auto-regulatory (21), possibly mediated by the binding of SarA to its own promoter. The binding affinity of SarR to a sarA promoter fragment is higher than its SarA counterpart (40), consistent with the idea that an activation motif might be present on the SarA protein but not on the SarR protein, and that SarR may repress by a simple competitive displacement mechanism. A second possibility is that SarA and SarR may form a hetero-dimer to interfere with the function of the SarA homo-dimer. Due to the conservation of residues involved in the dimerization, this could happen in vivo. Finally, SarR may function similarly to the bacteriophage lambda repressor (which also has a helix-turn-helix DNA binding motif). In this case, a slight DNA binding site difference (one base pair shift) could turn an activator to a repressor by affecting the RNA polymerase binding (7).

Figure 12B:
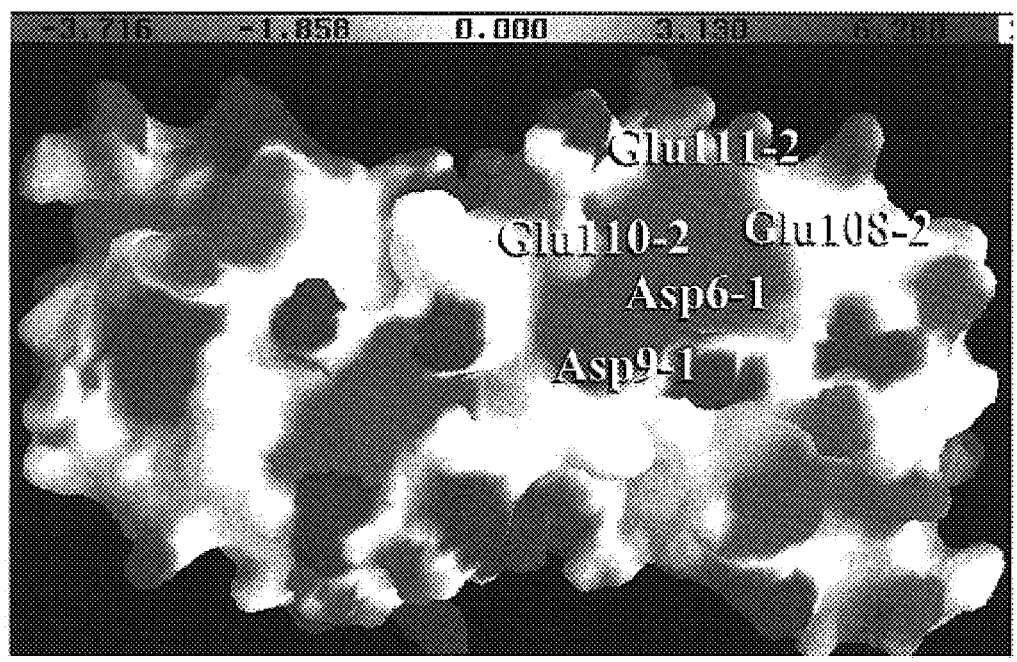

The structure of the SarR protein, combined with the sequence alignment of additional SarA family members (FIG. 11), shows that the regulatory mechanism is complicated. Residues 7, 8, and 11 appear to be important residues in the activation domain. When compared to the CAP, there is no isolated activation domain in the SarR dimeric structure, a calculation of the surface electronic potential revealed two negatively charged patches on the convex side of the SarR dimer (FIG. 12B). These patches include residues Asp6 and Asp9 from molecule 1, Glu108, Glu110, and Glu111 from molecule 2. Many transcription regulators work by binding DNA and then interacting with a component of the RNA polymerase machinery (52). For example, CAP regulates downstream protein expression mostly through its interactions with the C-terminal domains of alpha subunit of RNA polymerase (28). These acidic patches on the surface of SarR may represent activation motifs that allow SarR to regulate gene expression in a similar way. Since Glu108, Glu110, and Glu111 are not conserved among the SarA family (FIG. 11), this activity may have a different specificity among the family members. In this regard, we have determined that SarR, besides interacting with the sarA promoter, also directly binds to the hla promoter (e.g. alpha hemolysin gene), thus bypassing the effect of sarA in controlling target genes.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

REFERENCES

1. Adhya, S. and M. Gottesman. (1981) *Cell* 29:939-944.
2. Bayer, M. G., J. H. Heinrichs, and A. L. Cheung. (1996) *J. Bacteriol.* 178:4563-4570.
3. Blake, M. S., K. H. Johnston, G. J. Russell-Jones, and E. C. Gotschlich. (1984) *Anal. Biochem.* 136:175-179.
4. Boyce, J. M. (1997) Epidemiology and prevention of nosocomial infections. In: *The staphylococci in human disease*, edited by Crossley, K. B. and Archer, G. L. New York, N.Y.: Churchill Livingstone, 1997, p. 309-329.
5. Bradford, M. M. (1976) *Anal. Biochem.* 72:248
6. Brunger, A. T., Adams, P. D., Clore, G. M., Delano, W. L., Gros, P., Grosse-Kunstleve, R. W., Jiang, J.-S., Kuszewsk, J., Nilges, N., Pannu, N. S., Read, R. J., Rice, L. M., Simonson, T., and Warrrn, G. L. (1998) *Acta Cryst.* D54, 905-92.
7. Bushman, F. D. (1992) *Curr. Biol.* 2:673-675.
8. Carson, M. (1991) *J. appl. Crystallogr.* 24, 958-961.
9. Chan, P. F. and S. J. Foster. (1998) *J. Bacteriol.* 180: 6232-6241.
10. Cheung, A. L., M. G. Bayer, and J. H. Heinrichs. (1997) 179:3963-3971.
11. Cheung, A. L., Y. T. Chien, and A. S. Bayer. (1999) 67:1331-1337.
12. Cheung, A. L., K. Eberhardt, and V. A. Fischetti. (1994) *Anal. Biochem.* 222:511-514.
13. Cheung, A. L., K. Eberhardt, and J. H. Heinrichs. (1997) *Infect. Immun.* 2243-2249.
14. Cheung, A. L. and V. A. Fischetti. (1990) *J. Infect. Dis.* 161:1177-1186.
15. Cheung, A. L., J. M. Koomey, C. A. Butler, S. J. Projan, and V. A. Fischetti. (1992) *Proc. Natl. Acad. Sci. USA.* 89:6462-6466.
16. Cheung, A. L., M. Krishnan, E. A. Jaffe, and V. A. Fischetti. (1991) *J. Clin. Invest.* 87:2236-2245.
17. Cheung A. L., Schmidt, K., Bateman, B., & Manna, A. C. (2001) *Infection and Immunity* (under review).
18. Cheung, A. L. and S. J. Projan. (1994) *J. Bacteriol.* 176:4168-4172.
19. Chien, C.-T., A. C. Manna, S. J. Projan, and A. L. Cheung. (1999) *J. Biol. Chem.* 274:37169-37176.
20. Chien, Y. T., A. C. Manna, and A. L. Cheung. (1998) *Mol. Microbiol.* 31:991-1001.
21. Chien, Y. and A. L. Cheung. (1998) *J. Biol. Chem.* 237:2645-2652.
22. Doran, J. E. and R. H. Raynor. (1981) *Infect. Immun.* 33:683-689.
23. Gajiwala, K. S., Burley, S. K. (2000) *Current Opinion in Structural Biology*, 10:110-116.
24. Gajiwala, K. S., Chen, H., Cornille, F., Roques, B. P., Reith, W., Mach, B., Burley, S. K. (2000) *Nature* 403 (6772):916-21.
25. Hale, T. L. (1991) *Microbiol. Rev.* 55:206-224.
26. Heim, R., A. B. Cubitt, and R. Y. Tsien. (1995) *Nature* 373:663-664.
27. Holm, L., Sander, C. (1993) *J. Mol. Biol.* 233,123-138.
28. Ishihama, A. (1993) *J. Bacterial.* 175:2483.
29. Ishikawa, (2000) *Microbiology and Immunology*, 44(2): 97-104.
30. Janzon, L. and S. Arvidson. (1990) *EMBO. J.* 9:1391-1399.
31. Ji, G., R. Beavis, and R. P. Novick. (1997) *Science* 276:2027-2030.
32. Jones, K. F., B. N. Manjula, K. H. Johnston, S. K. Hollingshead, J. R. Scott, and V. A. Fischetti. (1985) *J. Exp. Med* 161:623-628.
33. Jones, T. A., Zou, J.-Y., Cowan, S. & Kjeldgaard, M. (1991) *Acta Cryst.* A47, 110-119.
34. Kornblum, J., B. Kreiswirth, S. J. Projan, H. Ross, and R. P. Novick. (1990) *Agr*: A polycistronic locus regulating exoprotein synthesis in *Staphylococcus aureus*, p. 373-402. In R. P. Novick (ed.), Molecular biology of the staphylococci, VCH Publishers, New York.
35. Laskowski, R. A., MacArthur, M. W., Moss, D. S. & Thornton, J. M. (1993) *J. Appl. Crystallogr.* 26, 283-291.
36. Lee, C. Y. (1992) *Mol. Microbiol.* 6:1515-1522.
37. Mahmood, R. and S. A. Khan. (1990) *J. Biol. Chem.* 265:4652-4656.
38. Maniatis, T., E. F. Fritsch, and J. Sambrook. (1989) Molecular cloning, a laboratory manual, Cold Spring Harbor Laboratory, Cold Spring Harbor, N.Y.
39. Manna, A. C., M. G. Bayer, and A. L. Cheung. (1998) *J. Bacteriol.* 180:3828-3836.
40. Manna, A. C. & Cheung, A. L. (2001) *Infect. Immun.* 69, 885-886.
41. Mayville, P. G. Ji, R. Beavis, H. Yang, M. Goger, R. P. Novick, and T. W. Muir. (1999) *Proc. Natl. Acad. Sci. U.S.A.* 96:1218-1223.
42. McDevitt, D., P. Francois, P. Vaudaux, and T. J. Foster. (1994) *Mol. Microbiol.* 11:237-248.
43. Miyazaki, E., J. M. Chen, C. Ko, and W. R. Bishai. (1999) *J. Bacteriol.* 181:2846-2851.
44. Morfeldt, E., D. Taylor, A. von Gabain, and S. Arvidson. (1995) *EMBO. J.* 14:4569-4577.
45. Navaza, J. (1994) *Acta Cryst.* A50, 157-163.
46. Nicholls, A., Sharp, K. A., Honig, B. (1991) *Proteins Struct. Funct. Genet.* 11:281.
47. Novick, R. P. (1990) The staphylococcus as a molecular genetic system, p. 1-40. In R. P. Novick (ed.), Molecular biology of the *staphylococci*, VCH, New York.
48. Novick, R. P. (1991) *Methods Enzymol.* 204:587-636.
49. Novick, R. P., H. F. Ross, S. J. Projan, J. Kornblum, B. Kreiswirth, and S. Moghazeh. (1993) *EMBO. J.* 12:3967-3977.
50. Otwinowski, Z., Minor, W. (1997) *Methods Enzymol* 276: 307-326.
51. Projan, S. J. and R. P. Novick. (1997) The molecular basis of pathogenicity, p. 55-81. In K. B. Crossley and G. L. Archer (ed.), The *staphylococci* in human diseases.
52. Ptashne M, Gann A. (1997) *Nature.* 386(6625):569-77.
53. Quiocho, F. A., Spurlino, J. C., Rodseth, L. E. (1997) *Structure*, 5, 997.
54. Rechtin, T. M., A. F. Gillaspy, M. A. Schumacher, R. G. Brennan, M. S. Smeltzer, and B. K. Hurlburt. (1999) *Mol. Microbiol.* 33:307-316.
55. Rost, B., C. Sander, and R. Schneider. (1994) *Comput. Appl. Biosci.* 10:53-60.
56. Russo-Marie, F., M. Roederer, B. Sager, L. A. Herzenberg, and D. Kaiser. (1998) *Proc. Natl. Acad. Sci. U.S.A.* 90:8194-8198.
57. Sau, S., L. Sun, and C. Y. Lee. (1997) *J. Bacteriol.* 179:1614-1621.
58. Schenk, S. and R. A. Laddaga. (1992) *FEMS Microbiol. Lett.* 94:133-138.
59. Schultz, S. C., Shields, G. C., Steitz, T. A. (1991) *Science*, 253:1001-1007.
60. Tegmark, K., Karlsson, A., & Arvidson, S. (2000) *Mol. Microbiol.* 37, 398-409.
61. Towbin, H., T. Staehelin, and J. Gordon. (1979) *Proc. Natl. Acad. Sci. USA:* 76:4350-4354.

What is claimed is:

1. An isolated nucleic acid molecule which regulates the expression of virulence determinants in gram positive bacteria, wherein said isolated nucleic acid molecule comprises the sequence set forth in SEQ ID NO:1.

2. The nucleic acid molecule of claim 1, wherein the bacteria is *Staphylococcus* species.

3. The isolated nucleic acid molecule of claim 2, wherein the bacterium is *Staphylococcus aureus*.

4. A vector comprising the isolated nucleic acid molecule of claim 3.

5. An isolated host cell comprising the vector of claim 4.

* * * * *

SEQUENCE LISTING

<160> NUMBER OF SEQ ID NOS: 35

<210> SEQ ID NO 1
<211> LENGTH: 947
<212> TYPE: DNA
<213> ORGANISM: Staphylococcus aureus
<220> FEATURE:
<221> NAME/KEY: CDS
<222> LOCATION: (208)..(552)
<223> OTHER INFORMATION:

<400> SEQUENCE: 1

```
gttttcaaaa tcggtggagg tgcatgaaaa agttattggg cattttttga aaataaaaaa    60
atatcaataa gttggagtca ttaccgaatt tttatactta tttgtttaga atgaacttta   120
taacatagtt ggatagagtt ttcgatttaa tacattaaat gtgaaccttg ctacaacaag   180
atgtgcatca gaaggagtgg tttaata atg agt aaa att aat gat att aat gat    234
                                Met Ser Lys Ile Asn Asp Ile Asn Asp
                                  1               5 tta gtc aac gca aca ttt caa gtt aag aag ttt ttc aga gat aca aaa      282
Leu Val Asn Ala Thr Phe Gln Val Lys Lys Phe Phe Arg Asp Thr Lys
 10                  15                  20                  25 aag aag ttc aat ttg aac tat gaa gaa att tat att tta aat cat att      330
Lys Lys Phe Asn Leu Asn Tyr Glu Glu Ile Tyr Ile Leu Asn His Ile
                 30                  35                  40 tta aga agt gag tct aac gaa atc tca tct aaa gag att gct aag tgc      378
Leu Arg Ser Glu Ser Asn Glu Ile Ser Ser Lys Glu Ile Ala Lys Cys
             45                  50                  55 tca gag ttc aaa cct tac tat tta act aaa gct tta caa aag cta aaa      426
Ser Glu Phe Lys Pro Tyr Tyr Leu Thr Lys Ala Leu Gln Lys Leu Lys
         60                  65                  70 gat tta aaa ttg tta tca aag aaa aga agt tta caa gac gaa aga aca      474
Asp Leu Lys Leu Leu Ser Lys Lys Arg Ser Leu Gln Asp Glu Arg Thr
     75                  80                  85 gtt att gtt tat gtt aca gat aca caa aaa gca aat att caa aaa ctg      522
Val Ile Val Tyr Val Thr Asp Thr Gln Lys Ala Asn Ile Gln Lys Leu
 90                  95                 100                 105 att tca gaa tta gaa gaa tac att aaa aat taaatcaagg ttaattgcgt        572
Ile Ser Glu Leu Glu Glu Tyr Ile Lys Asn
                110                 115 ttaataacat tgaacgataa caatttatta atacgaagtt atttattcag cattgggaca   632
taaaattaac ttaaaattta aatattgaag atgctttaat taaagttaaa gaccagccat   692
accttatttc agcttattaa gcttgacaca aggtacacta gtcttttat tttaatattt    752 tcttagaaaa tcaagtttac gatcataaat attttctgcg atatagcttt ggatggttcc   812
aagtattttc tctataattt gtgtgcgata agcaaaaatt ctaactgcaa aaccatgtgt   872
aggcaattga gaaatagcaa cacgacaatc ggatgtattg ctataagaac taatggtttc   932
ataaactgaa tcgat                                                   947
```

<210> SEQ ID NO 2
<211> LENGTH: 115
<212> TYPE: PRT
<213> ORGANISM: Staphylococcus aureus

<400> SEQUENCE: 2

```
Met Ser Lys Ile Asn Asp Ile Asn Asp Leu Val Asn Ala Thr Phe Gln
  1               5                  10                  15
```

```
Val Lys Lys Phe Phe Arg Asp Thr Lys Lys Phe Asn Leu Asn Tyr
         20                  25                  30

Glu Glu Ile Tyr Ile Leu Asn His Ile Leu Arg Ser Glu Ser Asn Glu
         35                  40                  45

Ile Ser Ser Lys Glu Ile Ala Lys Cys Ser Glu Phe Lys Pro Tyr Tyr
 50                  55                  60

Leu Thr Lys Ala Leu Gln Lys Leu Lys Asp Leu Lys Leu Leu Ser Lys
65                   70                  75                  80

Lys Arg Ser Leu Gln Asp Glu Arg Thr Val Ile Val Tyr Val Thr Asp
                 85                  90                  95

Thr Gln Lys Ala Asn Ile Gln Lys Leu Ile Ser Glu Leu Glu Glu Tyr
             100                 105                 110

Ile Lys Asn
        115
```

<210> SEQ ID NO 3
<211> LENGTH: 124
<212> TYPE: PRT
<213> ORGANISM: Staphylococcus aureus

<400> SEQUENCE: 3

```
Met Ala Ile Thr Lys Ile Asn Asp Cys Phe Glu Leu Leu Ser Met Val
1                5                  10                  15

Thr Tyr Ala Asp Lys Leu Lys Ser Leu Ile Lys Lys Glu Phe Ser Ile
             20                  25                  30

Ser Phe Glu Glu Phe Ala Val Leu Thr Tyr Ile Ser Glu Asn Lys Glu
         35                  40                  45

Lys Glu Tyr Tyr Leu Lys Asp Ile Ile Asn His Leu Asn Tyr Lys Gln
     50                  55                  60

Pro Gln Val Val Lys Ala Val Lys Ile Leu Ser Gln Glu Asp Tyr Phe
65                   70                  75                  80

Asp Lys Lys Arg Asn Glu His Asp Glu Arg Thr Val Leu Ile Leu Val
                 85                  90                  95

Asn Ala Gln Gln Arg Lys Lys Ile Glu Ser Leu Leu Ser Arg Val Asn
             100                 105                 110

Lys Arg Ile Thr Glu Ala Asn Asn Glu Ile Glu Leu
        115                 120
```

<210> SEQ ID NO 4
<211> LENGTH: 30
<212> TYPE: DNA
<213> ORGANISM: Artificial Sequence
<220> FEATURE:
<223> OTHER INFORMATION: Degenerate oligonucleotide.

<400> SEQUENCE: 4
atgwswaaaa tyaaygatat yaaygatttt                                           30

<210> SEQ ID NO 5
<211> LENGTH: 30
<212> TYPE: DNA
<213> ORGANISM: Artificial Sequence
<220> FEATURE:
<223> OTHER INFORMATION: Degenerate oligonucleotide.

<400> SEQUENCE: 5
attwswytcw swwckyaara trtgrttyaa                                           30

<210> SEQ ID NO 6

```
<211> LENGTH: 24
<212> TYPE: DNA
<213> ORGANISM: Artificial Sequence
<220> FEATURE:
<223> OTHER INFORMATION: Synthetic oligonucleotide.

<400> SEQUENCE: 6
gcatgaaaaa gatatcgggc attt                                              24

<210> SEQ ID NO 7
<211> LENGTH: 26
<212> TYPE: DNA
<213> ORGANISM: Artificial Sequence
<220> FEATURE:
<223> OTHER INFORMATION: Synthetic oligonucleotide.

<400> SEQUENCE: 7
gtgagtctaa cgatatctca tctaaa                                            26

<210> SEQ ID NO 8
<211> LENGTH: 14
<212> TYPE: PRT
<213> ORGANISM: Staphylococcus aureus
<220> FEATURE:
<221> NAME/KEY: MISC_FEATURE
<222> LOCATION: (1)..(1)
<223> OTHER INFORMATION: "X" is defined as any amino acid residue.
<220> FEATURE:
<221> NAME/KEY: MISC_FEATURE
<222> LOCATION: (13)..(13)
<223> OTHER INFORMATION: "X" is defined as being either S or T.

<400> SEQUENCE: 8

Xaa Lys Ile Asn Asp Ile Asn Asp Leu Val Asn Ala Xaa Phe
1               5                   10

<210> SEQ ID NO 9
<211> LENGTH: 8
<212> TYPE: DNA
<213> ORGANISM: Staphylococcus aureus

<400> SEQUENCE: 9 aggagtgg                                                                8

<210> SEQ ID NO 10
<211> LENGTH: 6
<212> TYPE: DNA
<213> ORGANISM: Staphylococcus aureus

<400> SEQUENCE: 10 tagaat                                                                  6

<210> SEQ ID NO 11
<211> LENGTH: 6
<212> TYPE: DNA
<213> ORGANISM: Staphylococcus aureus

<400> SEQUENCE: 11 ttaccg                                                                  6

<210> SEQ ID NO 12
<211> LENGTH: 20
<212> TYPE: DNA
<213> ORGANISM: Staphylococcus aureus

<400> SEQUENCE: 12
```
ttactaaatt aaaaaaatta                                          20

<210> SEQ ID NO 13
<211> LENGTH: 28
<212> TYPE: DNA
<213> ORGANISM: Staphylococcus aureus

<400> SEQUENCE: 13
taaattaatg ttatttttta ataattta                                 28

<210> SEQ ID NO 14
<211> LENGTH: 8
<212> TYPE: DNA
<213> ORGANISM: Staphylococcus aureus

<400> SEQUENCE: 14 taaattaa                                                        8

<210> SEQ ID NO 15
<211> LENGTH: 8
<212> TYPE: DNA
<213> ORGANISM: Staphylococcus aureus

<400> SEQUENCE: 15 ataattta                                                        8

<210> SEQ ID NO 16
<211> LENGTH: 8
<212> TYPE: DNA
<213> ORGANISM: Staphylococcus aureus

<400> SEQUENCE: 16 taaattat                                                        8

<210> SEQ ID NO 17
<211> LENGTH: 20
<212> TYPE: DNA
<213> ORGANISM: Staphylococcus aureus

<400> SEQUENCE: 17
ttactaaatt aaaaaaatta                                          20

<210> SEQ ID NO 18
<211> LENGTH: 49
<212> TYPE: DNA
<213> ORGANISM: Staphylococcus aureus

<400> SEQUENCE: 18
tcttaagacc taaattaatg ttatttttta ataatttaca ccaaattaa           49

<210> SEQ ID NO 19
<211> LENGTH: 210
<212> TYPE: DNA
<213> ORGANISM: Staphylococcus aureus

<400> SEQUENCE: 19
gttttcaaaa tcggtggagg tgcatgaaaa agttattggg cattttttga aaataaaaaa    60
atatcaataa gttggagtca ttaccgaatt tttatactta tttgtttaga atgaacttta   120
taacatagtt ggatagagtt ttcgatttaa tacattaaat gtgaaccttg ctacaacaag   180
atgtgcatca gaaggagtgg tttaataatg                                   210

-continued

<210> SEQ ID NO 20
<211> LENGTH: 29
<212> TYPE: DNA
<213> ORGANISM: Staphylococcus aureus

<400> SEQUENCE: 20
ctaaattaat gttattttt aataattta                                29

<210> SEQ ID NO 21
<211> LENGTH: 3
<212> TYPE: DNA
<213> ORGANISM: Staphylococcus aureus

<400> SEQUENCE: 21 aaa                                                           3

<210> SEQ ID NO 22
<211> LENGTH: 20
<212> TYPE: DNA
<213> ORGANISM: Staphylococcus aureus

<400> SEQUENCE: 22
aattaccttg tattgtcgat                                         20

<210> SEQ ID NO 23
<211> LENGTH: 22
<212> TYPE: DNA
<213> ORGANISM: Staphylococcus aureus

<400> SEQUENCE: 23
aaggtaaatt ataaaaaatg ct                                      22

<210> SEQ ID NO 24
<211> LENGTH: 8
<212> TYPE: DNA
<213> ORGANISM: Staphylococcus aureus

<400> SEQUENCE: 24 cagaaata                                                      8

<210> SEQ ID NO 25
<211> LENGTH: 25
<212> TYPE: DNA
<213> ORGANISM: Staphylococcus aureus

<400> SEQUENCE: 25
atcactgtgt ctaatgaata atttg                                   25

<210> SEQ ID NO 26
<211> LENGTH: 120
<212> TYPE: PRT
<213> ORGANISM: Artificial Sequence
<220> FEATURE:
<223> OTHER INFORMATION: Consensus sequence.
<220> FEATURE:
<221> NAME/KEY: MISC_FEATURE
<222> LOCATION: (2)..(2)
<223> OTHER INFORMATION: "X" is defined as any amino acid residue.
<220> FEATURE:
<221> NAME/KEY: MISC_FEATURE
<222> LOCATION: (4)..(4)
<223> OTHER INFORMATION: "X" is defined as any amino acid residue.
<220> FEATURE:
<221> NAME/KEY: MISC_FEATURE
<222> LOCATION: (10)..(10)
<223> OTHER INFORMATION: "X" is defined as any amino acid residue.
<220> FEATURE:

```
<221> NAME/KEY: MISC_FEATURE
<222> LOCATION: (15)..(17)
<223> OTHER INFORMATION: "X" is defined as any amino acid residue.
<220> FEATURE:
<221> NAME/KEY: MISC_FEATURE
<222> LOCATION: (19)..(20)
<223> OTHER INFORMATION: "X" is defined as any amino acid residue.
<220> FEATURE:
<221> NAME/KEY: MISC_FEATURE
<222> LOCATION: (24)..(25)
<223> OTHER INFORMATION: "X" is defined as any amino acid residue.
<220> FEATURE:
<221> NAME/KEY: MISC_FEATURE
<222> LOCATION: (31)..(31)
<223> OTHER INFORMATION: "X" is defined as any amino acid residue.
<220> FEATURE:
<221> NAME/KEY: MISC_FEATURE
<222> LOCATION: (38)..(38)
<223> OTHER INFORMATION: "X" is defined as any amino acid residue.
<220> FEATURE:
<221> NAME/KEY: MISC_FEATURE
<222> LOCATION: (44)..(45)
<223> OTHER INFORMATION: "X" is defined as any amino acid residue.
<220> FEATURE:
<221> NAME/KEY: MISC_FEATURE
<222> LOCATION: (47)..(47)
<223> OTHER INFORMATION: "X" is defined as any amino acid residue.
<220> FEATURE:
<221> NAME/KEY: MISC_FEATURE
<222> LOCATION: (51)..(52)
<223> OTHER INFORMATION: "X" is defined as any amino acid residue.
<220> FEATURE:
<221> NAME/KEY: MISC_FEATURE
<222> LOCATION: (58)..(59)
<223> OTHER INFORMATION: "X" is defined as any amino acid residue.
<220> FEATURE:
<221> NAME/KEY: MISC_FEATURE
<222> LOCATION: (61)..(61)
<223> OTHER INFORMATION: "X" is defined as any amino acid residue.
<220> FEATURE:
<221> NAME/KEY: MISC_FEATURE
<222> LOCATION: (73)..(73)
<223> OTHER INFORMATION: "X" is defined as any amino acid residue.
<220> FEATURE:
<221> NAME/KEY: MISC_FEATURE
<222> LOCATION: (77)..(78)
<223> OTHER INFORMATION: "X" is defined as any amino acid residue.
<220> FEATURE:
<221> NAME/KEY: MISC_FEATURE
<222> LOCATION: (86)..(87)
<223> OTHER INFORMATION: "X" is defined as any amino acid residue.
<220> FEATURE:
<221> NAME/KEY: MISC_FEATURE
<222> LOCATION: (95)..(95)
<223> OTHER INFORMATION: "X" is defined as any amino acid residue.
<220> FEATURE:
<221> NAME/KEY: MISC_FEATURE
<222> LOCATION: (97)..(97)
<223> OTHER INFORMATION: "X" is defined as any amino acid residue.
<220> FEATURE:
<221> NAME/KEY: MISC_FEATURE
<222> LOCATION: (99)..(99)
<223> OTHER INFORMATION: "X" is defined as any amino acid residue.
<220> FEATURE:
<221> NAME/KEY: MISC_FEATURE
<222> LOCATION: (102)..(102)
<223> OTHER INFORMATION: "X" is defined as any amino acid residue.
<220> FEATURE:
<221> NAME/KEY: MISC_FEATURE
<222> LOCATION: (106)..(106)
<223> OTHER INFORMATION: "X" is defined as any amino acid residue.
<220> FEATURE:
<221> NAME/KEY: MISC_FEATURE
<222> LOCATION: (110)..(110)
<223> OTHER INFORMATION: "X" is defined as any amino acid residue.
<220> FEATURE:
<221> NAME/KEY: MISC_FEATURE
<222> LOCATION: (114)..(114)
<223> OTHER INFORMATION: "X" is defined as any amino acid residue.
```

```
<220> FEATURE:
<221> NAME/KEY: MISC_FEATURE
<222> LOCATION: (117)..(118)
<223> OTHER INFORMATION: "X" is defined as any amino acid residue.
<220> FEATURE:
<221> NAME/KEY: MISC_FEATURE
<222> LOCATION: (120)..(120)
<223> OTHER INFORMATION: "X" is defined as any amino acid residue.

<400> SEQUENCE: 26

Met Xaa Met Xaa Lys Ile Asn Asp Ile Xaa Asp Leu Leu Asn Xaa Xaa
1               5                   10                  15

Xaa Tyr Xaa Xaa Lys Phe Lys Xaa Xaa Ile Lys Lys Glu Phe Xaa Leu
            20                  25                  30

Ser Phe Glu Glu Phe Xaa Ile Leu Thr Tyr Ile Xaa Xaa Gln Xaa Glu
        35                  40                  45

Asn Glu Xaa Xaa Leu Lys Asp Ile Ile Xaa Xaa Leu Xaa Tyr Lys Gln
    50                  55                  60

Pro Gln Leu Val Lys Ala Leu Lys Xaa Leu Lys Lys Xaa Xaa Tyr Leu
65                  70                  75                  80

Ser Lys Lys Arg Ser Xaa Xaa Asp Glu Arg Thr Val Leu Ile Xaa Val
                85                  90                  95

Xaa Asp Xaa Gln Arg Xaa Lys Ile Glu Xaa Leu Leu Ser Xaa Val Asn
            100                 105                 110

Gln Xaa Ile Lys Xaa Xaa Asn Xaa
        115                 120

<210> SEQ ID NO 27
<211> LENGTH: 119
<212> TYPE: PRT
<213> ORGANISM: Staphylococcus aureus

<400> SEQUENCE: 27

Met Lys Tyr Asn Asn His Asp Lys Ile Arg Asp Phe Ile Ile Ile Glu
1               5                   10                  15

Ala Tyr Met Phe Arg Phe Lys Lys Val Lys Pro Glu Val Asp Met
            20                  25                  30

Thr Ile Lys Glu Phe Ile Leu Leu Thr Tyr Leu Phe His Gln Gln Glu
        35                  40                  45

Asn Thr Leu Pro Phe Lys Lys Ile Val Ser Asp Leu Cys Tyr Lys Gln
    50                  55                  60

Ser Asp Leu Val Gln His Ile Lys Val Leu Val Lys His Ser Tyr Ile
65                  70                  75                  80

Ser Lys Val Arg Ser Lys Ile Asp Glu Arg Asn Thr Tyr Ile Ser Ile
                85                  90                  95

Ser Glu Glu Gln Arg Glu Lys Ile Ala Glu Arg Val Thr Leu Phe Asp
            100                 105                 110

Gln Ile Ile Lys Gln Phe Asn
        115

<210> SEQ ID NO 28
<211> LENGTH: 118
<212> TYPE: PRT
<213> ORGANISM: Staphylococcus aureus

<400> SEQUENCE: 28

Ser Gln Met Ile Pro Lys Asp Ser Lys Glu Phe Leu Asn Leu Met Met
1               5                   10                  15

Tyr Thr Met Tyr Phe Lys Asn Ile Ile Lys Lys His Leu Thr Leu Ser
```

-continued

```
                    20                  25                  30
Phe Val Glu Phe Thr Ile Leu Ala Ile Ile Thr Ser Gln Asn Lys Asn
            35                  40                  45
Ile Val Leu Leu Lys Asp Leu Ile Glu Thr Ile His His Lys Tyr Pro
        50                  55                  60
Gln Thr Val Arg Ala Leu Asn Asn Leu Lys Lys Gln Gly Tyr Leu Ile
65                  70                  75                  80
Lys Glu Arg Ser Thr Glu Asp Glu Arg Lys Ile Leu Ile His Met Asp
                85                  90                  95
Asp Ala Gln Gln Asp His Ala Glu Gln Leu Leu Ala Gly Val Asn Gln
            100                 105                 110
Leu Leu Ala Asp Lys Asp
        115

<210> SEQ ID NO 29
<211> LENGTH: 13
<212> TYPE: PRT
<213> ORGANISM: Staphylococcus aureus

<400> SEQUENCE: 29

Asp Val Thr Gly Arg Ile Ala Gln Thr Leu Leu Asn Leu
1               5                   10

<210> SEQ ID NO 30
<211> LENGTH: 6
<212> TYPE: PRT
<213> ORGANISM: Staphylococcus aureus

<400> SEQUENCE: 30

Gln Ile Lys Ile Thr Arg
1               5

<210> SEQ ID NO 31
<211> LENGTH: 6
<212> TYPE: PRT
<213> ORGANISM: Staphylococcus aureus

<400> SEQUENCE: 31

Glu Ile Gly Gln Ile Val
1               5

<210> SEQ ID NO 32
<211> LENGTH: 28
<212> TYPE: PRT
<213> ORGANISM: Staphylococcus aureus

<400> SEQUENCE: 32

Cys Ser Arg Gln Thr Val Gly Arg Ile Leu Lys Met Leu Glu Asp Gln
1               5                   10                  15

Asn Leu Ile Ser Ala His Gly Lys Thr Ile Val Val
            20                  25

<210> SEQ ID NO 33
<211> LENGTH: 3
<212> TYPE: DNA
<213> ORGANISM: Staphylococcus aureus

<400> SEQUENCE: 33 atg                                                                    3

<210> SEQ ID NO 34
```

```
<211> LENGTH: 3
<212> TYPE: DNA
<213> ORGANISM: Staphylococcus aureus

<400> SEQUENCE: 34 taa                                                                      3

<210> SEQ ID NO 35
<211> LENGTH: 120
<212> TYPE: PRT
<213> ORGANISM: Staphylococcus aureus

<400> SEQUENCE: 35

Met Ala Ile Thr Lys Ile Asn Asp Cys Phe Glu Leu Leu Ser Met Val
1               5                   10                  15

Thr Tyr Ala Asp Lys Leu Lys Ser Leu Ile Lys Lys Glu Phe Ser Ile
            20                  25                  30

Ser Phe Glu Glu Phe Ala Val Leu Thr Tyr Ile Ser Glu Asn Lys Glu
        35                  40                  45

Lys Glu Tyr Tyr Leu Lys Asp Ile Ile Asn His Leu Asn Tyr Lys Gln
    50                  55                  60

Pro Gln Val Val Lys Ala Val Lys Ile Leu Ser Gln Glu Asp Tyr Phe
65                  70                  75                  80

Asp Lys Lys Arg Asn Glu His Asp Glu Arg Thr Val Leu Ile Leu Val
            85                  90                  95

Asn Ala Gln Gln Arg Lys Lys Ile Glu Ser Leu Leu Ser Arg Val Asn
            100                 105                 110

Lys Arg Ile Thr Glu Ala Asn Asn
        115                 120
```